US007547547B2

(12) United States Patent
Dang et al.

(10) Patent No.: US 7,547,547 B2
(45) Date of Patent: Jun. 16, 2009

(54) BIOPROCESS FOR PRODUCING UNIFORM EMBRYOID BODIES FROM EMBRYONIC STEM CELLS IN A HIGH DENSITY BIOREACTOR

(75) Inventors: Stephen Dang, North York (CA); Peter W. Zandstra, 84 Alcina Avenue, Toronto, Ontario (CA) M6G 2E6

(73) Assignee: Peter W. Zandstra, Toronto (CA)

( * ) Notice: Subject to any disclaimer, the term of this patent is extended or adjusted under 35 U.S.C. 154(b) by 280 days.

(21) Appl. No.: 10/189,642

(22) Filed: Jul. 3, 2002

(65) Prior Publication Data

US 2003/0119107 A1 Jun. 26, 2003

Related U.S. Application Data

(60) Provisional application No. 60/302,706, filed on Jul. 5, 2001.

(30) Foreign Application Priority Data

Jul. 4, 2001 (CA) .................................. 2351156

(51) Int. Cl.
*C12N 5/00* (2006.01)
*C12N 5/02* (2006.01)
*C12N 15/00* (2006.01)

(52) U.S. Cl. ...................... 435/382; 435/377; 435/325; 435/320.1

(58) Field of Classification Search ................. 435/325, 435/363, 366, 374, 377, 404, 405, 395, 382, 435/320.1
See application file for complete search history.

(56) References Cited

U.S. PATENT DOCUMENTS 5,073,491 A 12/1991 Familletti .................... 435/240
2003/0175954 A1* 9/2003 Shamblott et al. ........... 435/366

OTHER PUBLICATIONS

Zandstra et al. Blood, 94(10), Supplement 1, Part 2, pp. 351b, Nov. 15, 1999, Abstract #4795 only.*
Seifert et al. Biotech. Prog, 13:569-576 (1997).*
Ling et al. J. of Cell. Physio., 171:104-115 (1997).*
O'Shea. The Anatomical Record (New Anat.), 257: 32-41 (1999).*
Cai et al. BMC Dev. Bio., 5: 26, 1-7, 2005.*
M. Wartenberg et al., *Laboratory Investigation*, vol. 78, No. 10, Oct. 1998, pp. 1301-1314.
Y. Sukai et al., *Cell Transplantation*, vol. 8, No. 5, 1999, pp. 531-541.
K. K. Papas et al., *Cytotechnology*, vol. 13, No. 1, 1993, pp. 1-12.
N. C. Cosby et al., *J. Reprod. and Fert*, vol. 90, No. 1, 1990, pp. 19-24.
J. P. Magyar et al., *Annals of the New York Academy of Sciences*, vol. 944, Nov. 2001, pp. 135-143.
S. M. Dang et al., *Biotechnology and Bioengineering*, vol. 78, No. 4, May 20, 2002, pp. 442-453.
S. Assay et al., *Diabetes*, vol. 50, Aug. 2001, pp. 1691-1697.
G. Bain et al., *Dev Biol* 168, 1995, pp. 342-357.
G. Bain et al., *Biochem Biophys Res Commun* 223, 1996, pp. 691-694.
R. S. Beddington et al., *Development* 105, 1989, pp. 733-737.
C. R. Bjornson et al., *Science* 283, Jan. 22, 1999, pp. 534-537.
C. Brink et al., *Mech Devel* 100, 2001, pp. 37-43.
C. A. Burdsal et al., *Development* 118, 1993, pp. 829-844.
U. Chen et al., *Proc Natl Acad Sci USA*, vol. 89, Apr. 1992, pp. 2541-2545.
K. Choi et al., *Development* 125, 1998, pp. 725-732.
D. L. Clarke et al., *Science*, vol. 288, Jun. 2, 2000, pp. 1660-1663.
C. Dani et al., *J Cell Sci* 110, 1997, pp. 1279-1285.
M. C. Dickson et al., *Development* 117, 1993, pp. 625-639.
J. Dinsmore et al., *Cell Transplantation*, vol. 5, No. 2, 1996, pp. 131-143.
T. C. Doetschman et al., *J Embroyol Exp Morph* 87, 1985, pp. 27-45.
A. Eichmann et al., *Proc Natl Acad Sci USA*, vol. 94, May 1997, pp. 5141-5146.
M. J. Evans et al., *Nature*, vol. 292, Jul. 9, 1981, pp. 154-156.
M. Fleischmann et al., *FEBS Letters* 440, 1998, pp. 370-376.
M. Gannon et al., *Developmental Biology* 238, 2001, pp. 185-201.
G. J. Lieschke et al., *Experimental Hematology* 23, 1995, pp. 328-334.
S. Gory et al., *Blood*, vol. 93, No. 1, Jan. 1, 1999, pp. 184-192.
J. C. Gutierrez-Ramos et al., *Proc Natl Acad Sci USA*, vol. 89, Oct. 1992, pp. 9171-9175.
A. K. Hadjantonakis et al., *Mechanisms of Development* 76, 1998, pp. 79-90.
A. K. Hadjantonakis et al., *Histochem Cell Biol* 115, 2001, pp. 49-58.
D. J. Irvine et al., *J Biomed Mater Res* 40, Jun. 5, 1998, pp. 438-509.
A. Kalyani et al., *Developmental Biology* 186, 1997, pp. 202-223.
I. Kehat et al., *J Clin Invest*, vol. 108, No. 3, Aug. 2001, pp. 407-414.
G. M. Keller, *Curr Opin Cell Biology* 7, 1995, pp. 862-869.

(Continued)

*Primary Examiner*—Thaian N Ton
(74) *Attorney, Agent, or Firm*—Daniel A. Monaco; Drinker Biddle & Reath LLP

(57) ABSTRACT

The present inventors identified aggregation of embryonic stem cells and embryoid bodies (EBs) as the cause of the difficulty in generating large numbers of the embryonic stem cells (ES) cell-derived tissues. To counter this, the invention provides a novel bioprocess where aggregation of spheroid forming cells, such as embryonic stem cells and spheroids, such as EBs is controlled, such as by encapsulation of within a matrix. As a result, EBs can be generated with high efficiency and cultured in high cell density, well-mixed systems. Well-mixed conditions facilitate measurement and control of the bulk media conditions and allow for the use of scalable bioreactor systems for clinical production of tissue. Therefore, the invention enables generation of ES cell-derived tissue on a clinical scale. The invention is also applicable to any spheroid-forming cells and other types of pluripotent cells.

22 Claims, 10 Drawing Sheets

OTHER PUBLICATIONS

G. Keller et al., *Mol Cell Biol*, vol. 13, No. 1, Jan. 1993, pp. 473-486.
M. Kennedy et al., *Nature* 386, Apr. 3, 1997, pp. 488-493.
M. G. Klug et al., *J Clin Invest*, vol. 98, No. 1, Jul. 1996, pp. 216-224.
K. S. Ko et al., *J Cell Sci* 114, 2001, pp. 1155-1167.
L. Larue et al., *Development* 122, 1996, pp. 3185-3194.
M. Li et al., *Curr Biol* 8, 1998, pp. 971-974.
S. Levenberg et al., *Proc Natl Acad Sci USA*, vol. 99, No. 7, Apr. 2, 2002, pp. 4391-4396.
D. Ludwig et al., *Mammalian Genome* 11, 2000, pp. 1030-1033.
N. Lumelsky et al., *Science*, vol. 292, May 18, 2001, pp. 1389-1394.
E. Maltepe et al., *Nature*, vol. 386, Mar. 27, 1997, pp. 403-407.
E. Marshall, *Science* 287, 2000, pp. 1419-1421.
S. L. McKinney-Freeman et al., *Proc Natl Acad Sci USA*, vol. 99, No. 3, Feb. 5, 2002, pp. 1341-1346.
M. Muller et al., *FASEB Jour*, vol. 14, Dec. 2000, pp. 2540-2548.
C. Mummery et al., *Jour Anat* 200, 2002, pp. 233-242.
N. Nakayama et al., *Blood*, vol. 95, No. 7, Apr. 1, 2000, pp. 2275-2283.
A. Nagy et al., *Proc Natl Acad Sci USA*, vol. 90, Issue 18, Sep. 15, 1993, pp. 8424-8428.
J. Nichols et al., *Cell*, vol. 95, Oct. 30, 1998, pp. 379-391.
S. Okabe et al., *Mech Dev* 59, 1996, pp. 89-102.
R. Palacios et al., *Proc Natl Acad Sci USA*, vol. 92, Issue 16, Aug. 1, 1995, pp. 7530-7534.
T. A. Pelton et al., *Jour Cell Sci* 115, 2002, pp. 329-339.
A. C. Perkins, *Reprod Fertil Dev* 10, 1998, pp. 563-572.
V. K. Ramiya et al., *Nature Medicine*, vol. 6, No. 3, Mar. 2000, pp. 278-282.
P. D. Rathjen et al., *Reprod Fertil Dev* 10, 1998, pp. 31-47.
J. Rohwedel et al., *Dev Biol* 164, 1994, pp. 87-101.
B. E. Reubinoff et al., *Nat Biotechnol*, vol. 19, Dec. 2001, pp. 1134-1140.
C. Ryan et al., *Jour Clin Microbiology*, vol. 33, No. 7, Jul. 1995, pp. 1720-1726.
R. E. Schwartz et al., *Jour Clin Invest* vol. 109, No. 10, May 2002, pp. 1291-1302.
M. Schuldiner et al., *Proc Natl Acad Sci USA*, vol. 97, No. 21, Oct. 10, 2000, pp. 11307-11312.
M. Schuldiner et al., *Brain Research* 913, 2001, pp. 201-205.
M. V. Sefton et al., *Ann NY Acad Sci* 831, 1997, pp. 260-270.
H. G. Slager et al., *Dev Genet* 14, 1993, pp. 212-224.
S. B. Smith et al., *Jour Biol Chem*, vol. 275, No. 47, Nov. 24, 2000, pp. 36910-36919.
B. Soria, *Defferentiation* 68, 2000, pp. 205-219.
B. Soria et al., *Diabetologia* 44, 2001, pp. 407-415.
B. Soria et al., *Diabetes*, vol. 49, Feb. 2000, pp. 1-6.
A. Suzuki et al., *Jour Cell Biol*, vol. 156, No. 1, Jan. 7, 2002, pp. 173-184.
S. Tanaka et al., *Science*, vol. 282, Dec. 11, 1998, pp. 2072-2075.
J. A. Thomson et al., *Science*, vol. 282, Nov. 6, 1998, pp. 1145-1147.
J. A. Thomson et al., *Trends Biotechnol*, vol. 18, Feb. 2000, pp. 53-57.
J. G. Toma et al., *Nat Cell Biol*, vol. 3, Sep. 2001, pp. 778-784.
V. Tropepe et al., *Neuron*, vol. 30, Apr. 2001, pp. 65-78.
V. Tropepe et al., *Devel Biol* 208, 1999, pp. 166-188.
V. Turcanu et al., *Nature Medicine*, vol. 7, No. 3, Mar. 2001, pp. 373-376.
J. J. Vallbacka et al., *Jour Controlled Release* 72, 2001, pp. 93-100.
R. Wang et al., *Development* 114, 1992, pp. 303-316.
J. C. Weaver et al., *Biotechnology*, vol. 6, Sep. 1988, pp. 1084-1088.
M. V. Wiles et al., *Experimental Cell Research* 247, 1999, pp. 241-248.
M. V. Wiles et al., *Development* 111, 1991, pp. 259-267.
A. M. Wobus et al., *J Mol Cell Cardiol* 29, 1997, pp. 1525-1539.
J. Wu et al., *J Biol Chem*, vol. 264, No. 11, Apr. 15, 1989, pp. 6472-6479.
G. Yamada et al., *Biochem Biophys Res Commun*, vol. 199, No. 2, Mar. 15, 1994, pp. 552-563.
P. W. Zandstra et al., *Proc Natl Acad Sci USA*, vol. 94, Apr. 1997, pp. 4698-4703.
P. W. Zandstra et al., *Annu Rev Biomed Eng* 3, 2001, pp. 275-305.
P. W. Zandstra et al., *Blood*, vol. 96, No. 4, Aug. 15, 2000, pp. 1215-1222.

\* cited by examiner

BIOPROCESS FOR PRODUCING UNIFORM EMBRYOID BODIES FROM EMBRYONIC STEM CELLS IN A HIGH DENSITY BIOREACTOR

CROSS REFERENCE TO RELATED APPLICATIONS

This application hereby claims the benefit of priority from Canadian Patent Application No. 2,351,156 filed Jul. 4, 2001 and U.S. Provisional Patent Application No. 60/302,706 filed Jul. 5, 2001, both entitled, "A Bioprocess For The Generation Of Pluripotent Cell Derived Cells And Tissues". Both of these applications are herein incorporated by reference.

FIELD OF THE INVENTION

The invention relates to a process for generating cells and tissues, preferably cells and tissues derived from pluripotent cells or spheroid forming cells. In one embodiment the pluripotent cells are embryonic stem cells. Products and applications resulting from said process are also encompassed within the scope of this application.

BACKGROUND OF THE INVENTION

Tissue engineering, transplantation therapy, gene therapy, and drug discovery promise to revolutionize the medical paradigm and herald the coming of the "biotechnology era". However, development and implementation of these technologies depend upon cell-based approaches that require a plentiful supply of human cells: a supply that unfortunately does not currently exist. Therefore, identifying sources of human cells that can be practically obtained in sufficient quantities is of paramount importance. Spheroid forming cells, preferably pluripotent cells such as human embryonic stem cells (Thomson, Itskovitz-Eldor et al. 1998), neural stem cells (Clarke, Johansson, et al. 2000), multipotent adult progenitor cells (Schwartz, Reyes, et al. 2002), and others may be able to provide tissue in this manner.

The potential utility of pluripotent cells, in particular, the utility of embryonic stem (ES) cells, is derived from their demonstrated ability to differentiate into any other cell type in the body (Evans and Kaufman, 1981). Derived from the early embryo, ES cells can be grown and manipulated in vitro. ES cells are pluripotent cells that have the ability to differentiate into any cell type in the body (Evans and Kaufman 1981). They also have the ability to grow and multiply indefinitely while maintaining their pluripotentiality. Theoretically, these traits make ES cells an unlimited source of any cell type and therefore a very attractive tissue source for other biotechnological applications (Zandstra and Nagy 2001).

Generation of various differentiated cell types (cardiac myocytes, hematopoietic cells, neurons, hepatocytes, and others) from murine ES cells (e.g., Wang, Clark et al. 1992; Rohwedel, Maltsev et al. 1994; Bain, Kitchens et al. 1995; Palacios, Golunski et al. 1995; Choi, Kennedy et al. 1998; Fleischmann, Bloch et al. 1998; Tropepe, Sibilia et al. 1999) as well as from human ES cells (e.g., Jones and Thomson 2000; Thomson et al. 1998; Mummery et al 2002; Levenberg et al. 2002; Reubinoff et al. 2001; Assady et al 2001) has been extensively reported.

In general, production of these various cell types from ES cells require a complex multi-step process, starting with the expansion of ES cells to adequate numbers. Next, ES cells would be differentiated to the desired cell type(s). Finally, the desired cells would be selected and purified from the remaining cells before they could be utilized for various applications.

In vitro, differentiating ES cells follow a reproducible temporal pattern of development that in many ways recapitulates early embryogenesis (Keller 1995). As ES cells and their derivatives proliferate and differentiate, they typically form spherical tissue-like structures (spheroids) called Embryoid Bodies (EBs). Other pluripotent stem cells such as neural stem cells have also been described to form spheroids. In the case of neural stem cells these spheroids are termed neurospheres (Kalyani, Hobson, and Rao, 1997). In the case of ES cells, over time, EBs increase in cell number and complexity as cells from the three embryonic germ layers are formed (Keller 1995). The ability to control and manipulate the formation of spheroids from pluripotent cells and other types of cells that are derived directly, or indirectly from human tissue, as well as the interactions between the spheroids and between the spheroid-forming cells (i.e., prevent or inhibit the aggregation of spheroids) would allow for the control of interactions between these cells during proliferation and differentiation, and thus be an important development for the design of technologies for the in vitro differentiation of pluripotent cells. For example, the generation of "chimeric spheroids" or "chimeric EBs" defined as multicellular, spherical structure comprising a mixture of differentiated cells and pluripotent cells (Perkins, 1998), has been shown to be an effective approach to influence the development of the cell types in from pluripotent cells (Clarke, Johansson et al. 2000).

Current ES cell differentiation systems include cultures initiated with an ES cell suspension in liquid media (LSC), or methylcellulose (semi-solid) media (MC), or attached to a surface in liquid media, or with multi-ES cell aggregates formed in "hanging drop" cultures (HD) where ES cells are aggregated in hanging drops for 2 days before transfer to liquid culture (see FIG. 1). These systems are adequate for small-scale laboratory purposes but are not amenable to clinical production because of deficiency in three important areas: a) the ability to measure and control the extracellular environment, b) scalability, and c) cell density.

These systems are static and batch-style cultures that result in formation of spatial and temporal gradients in nutrients and metabolic products. These gradients make measurement and process control difficult because these processes depend on sampling measurements that need to reflect the conditions throughout the culture. The inability to control the cell culture enviroment will affect product purity and reproducibility, as well as the cell types that can be readily generated [e.g.; for oxygen (Maltepe, Schmidt, et al. 1997), glucose (Soira, 2001) and many other biological and physicochemical factors (Zandstra and Nagy, 2001)]. In the case of methylcellulose culture, the semi-solid media also hinders measurement and manipulation. Regulatory approval for the use of any biotechnology product demands consistency in the method of production and in the final product itself (http://www.fda.gov/cdrh/tisseng/te6.html). This is not possible when measurement and control are impeded or absent.

Second, clinical or industrial scale production of cells from the current culture systems is not practical. The current systems are typically carried out in petri dishes where cells grow in only a thin layer of media. These systems are essentially two-dimensional with respect to the EBs; therefore, unrealistically large surface areas would be required for industrial scale production. It can be estimated that several billion cells would be need for applications such as cardiac cell therapy (Zandstra and Nagy, 2001); this scale of cell production is highly impractical, if not impossible using current technologies.

Third, current liquid suspension cultures (LSC) require EBs to be cultured at relatively low density. Higher cell densities can be achieved in methylcellulose cultures, where semi-solid media reduces the likelihood of cell aggregation, however media supplementation of methylcellulose cultures is troublesome and increased cell density would demand more frequent supplementation.

Because of the limitations reviewed above, one ideal differentiation culture system for clinical scale production of EBs would be the stirred tank reactor or other scalable, well-mixed and controlled bioreactor systems such as a fluidized bed reactor. While the standard methods are limited to two-dimensional growth because of static conditions, a controlled bioreactor could suspend the cells evenly throughout the volume (in three-dimensions). This configuration of system can be easily scaled in size to accommodate the need for increased production of cells. In addition, stirring ensures homogenous media conditions throughout the reactor that would facilitate measurement and control of the extracellular environment.

Despite the importance of stirred or other well-mixed bioreactors, to date there have been no reports of successful use of these systems for ES cell differentiation culture. ES cells added directly to stirred culture quickly aggregate into large cell clumps within 24 hours and cell growth and differentiation within these clumps are severely impaired (Wartenberg et al. (1998)). Differentiation of ES cells in stirred culture is therefore a nontrivial task; however the ability to do so would greatly facilitate clinical and industrial scale production of cells for therapeutic purposes. ES cells cultured in stirred bioreactors fail to generate EBs in an efficient manner. Therefore, there is a need to develop methods for efficient growth and differentiation of spheroid forming cells, preferably pluripotent cells, such as ES cells.

SUMMARY OF THE INVENTION

This patent application is based upon a novel technology that overcomes one or more of the limitations of the prior art: a) the ability to measure and control the extracellular environment, b) scalability, and c) cell density and allows for the scalable generation of cells and.or tissue derived from spheroid-forming cell, preferably pluripotent, preferably ES cells.

The present inventors have determined that ES cells cultured in stirred bioreactors fail to generate EBs in an efficient manner because the cells aggregate forming large cell clumps that results in poor cell proliferation and incomplete cell differentiation. As such, in one aspect, the present invention provides a process to control cellular and spheroid aggregation of spheroid forming cells, such as ES cells or neuronal stem cells, to enable the use of a stirred tank reactor or other scalable, well-mixed and controlled bioreactor systems such as a fluidized bed reactor. The invention can also have benefits in other systems, especially liquid systems such as LSC.

In one embodiment, the invention provides a method of culturing differentiating pluripotent cells, preferably ES cells, in a bioreactor system by controlling cellular aggregation. Although a preferred embodiment of the invention is with ES cells, the invention is not limited to ES cell derived cells and tissues. It is equally applicable to any spheroid forming cell type, preferably pluripotent cell type that can differentiate as a cell cluster or aggregate, or form spheroid bodies, such as adult pluripotent cells (Schwartz, Reyes, et al. 2002; Clarke, Johansson et al. 2000) embryonic germ cells (EG cells) (reviewed in Thomson and Odorico, 2000), early primitive ectoderm-like cells (EPL) (Pelton and Sharma, 2002), and neuronal stem cells. As such the embodiments of the invention as outlined below in relation to embryonic stem cells also apply to other pluripotent cells where controlling aggregation of the cells at various points of expansion and or differentiation can enhance the efficiency of said expansion, spheroid formation or differentiation and are intended to be encompassed within the scope of the present invention.

In one embodiment, the invention provides a method of generating pluripotent cell derived cells comprising culturing pluripotent cells, such as ES cells, EG cells, EPL cells, and adult pluripotent cells (Schwartz, Reyes, et al. 2002), while controlling cellular and spheroid aggregation. In a preferred embodiment, the method is conducted under conditions that permit cell differentiation and proliferation. In another embodiment, the pluripotent cells are encapsulated to prevent aggregation with neighboring cells, spheroids or cells contained in separate capsules. In another embodiment the aggregation between specific cell types is controlled (to enable aggregation necessary for spheroid formation, where applicable) and the aggregation between spheroids of these cells is prevented. In yet another embodiment the kinetics of aggregation is controlled.

In one embodiment, the invention provides a method of generating embryonic stem cell derived cells comprising culturing embryonic stem cells under conditions that enable embryoid body formation and embryonic stem cell differentiation while controlling cell aggregation.

In a preferred embodiment, the embryonic stem cells are encapsulated to control cell aggregation such that each capsule will transiently contain and give rise to one embryoid body. In another embodiment, each capsule contains a predetermined number of ES cells that are permitted to aggregate and together give rise to a single EB. Preferably, the undifferentiated embryonic stem cells are first encapsulated to prevent aggregation between ES cells contained within separate capsules. Encapsulated embryonic stem cells are then cultured under conditions that enable cell proliferation and differentiation, leading to embryoid body formation. In a more preferred embodiment, emulsification of cells with agar in inert silicon oil is used to encapsulate the embryonic stem cells. In a most preferred embodiment, this emulsification results in the generation of agarose microcapsules containing embryonic stem cells. In yet another embodiment the process of encapsulation allows for the control of pluripotent cells aggregation by interfering with cell surface receptor binding. In a preferred embodiment, the process of encapsulation allows for the control of ES cell aggregation by interfering with E-cadherin mediated ES cell aggregation.

In another embodiment, the invention provides a method wherein the embryonic stem cells are cultured under conditions wherein embryoid bodies and/or differentiated embyronic stem cells can be formed. For example, some ES cell lines require aggregation of multiple ES cells to enable EB formation. Following these permissive steps, cells are transferred to conditions that prevent aggregation of embryoid bodies. In one embodiment, the method further comprises a step wherein the differentiated embryonic stem cells and/or tissues of interest are selected and harvested. In a preferred embodiment, the cells and/or tissues of interest are cardiomyocytes or cardiac tissue or hematopoietic cells or tissue or endothelial cells or tissues.

In another embodiment, the invention provides an embryonic stem cell derived cell culture obtained using the method of the invention. In a further embodiment, the invention provides embryonic stem cell derived cells and tissues obtained using the method of the invention.

In yet another embodiment the invention provides a method to identify factors, e.g. any variant, condition, substance, that affect embryonic stem cell differentiation and/or embryoid body formation, said method comprising culturing the embryonic stem cells while preventing embryoid body and embryonic stem cell aggregation, in the presence of the factor to be tested and then detecting the effect of the variant on embryonic stem cell differentiation and embryoid body formation. In a further embodiment, of said method, the effect on embryonic stem cell differentiation and embryoid body formation is compared to a control culture, preferably a negative control wherein embryonic stem cells are cultured under the same conditions except in the absence of the factor to be tested. The invention also provides a method of identifying factors that affect cell proliferation or differentiation in any cell culture by encapsulating said cells. The invention also encompassed a method of preventing cell aggregation in any cell type by encapsulation.

Other features and advantages of the present invention will become apparent from the following detailed description. For instance where reference is made to embryoid bodies or embryonic stem cells, the invention can also be applied to spheroid forming cells and spheroids. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 7 panel B is a linear graph illustrating aggregation kinetics of EBs differentiated for 0, 2, 4, and 6 days.

FIG. 8 panel B is a photograph series of differentiating ES cells forming EBs inside the agarose microcapsules. Day 0 shows encapsulated ES cells, day 2 shows day 2 EBs, day 4 shows EBs emerging, as desired, from the agarose microcapsules.

FIG. 9 panel A shows cells expressing Flk-1 (y-axis) and CD34 (x-axis). Cells expressing either Flk-1 or CD34 were gated and the percent of cells expressing these markers is indicated. FIG. 9 panel B shows CD31 expression by ungated cells. FIG. 9 panel C shows CD31 expression by gated cells. CD34 and/or Flk-1 expression together with CD31 expression identifies endothelial cells.

FIG. 10 panel B shows morphologic and structural analysis of bioreactor-grown ES cell-derived cardiomyocytes. The cells exhibit a mature sarcomeric organization and Z-banding (arrow). FIG. 10 panel C shows a cross section of a "cardiac body" (a spheroid of ES cell derived cardiac cells) generated in bioreactors.

DETAILED DESCRIPTION OF THE INVENTION

Definitions

Figure 1:
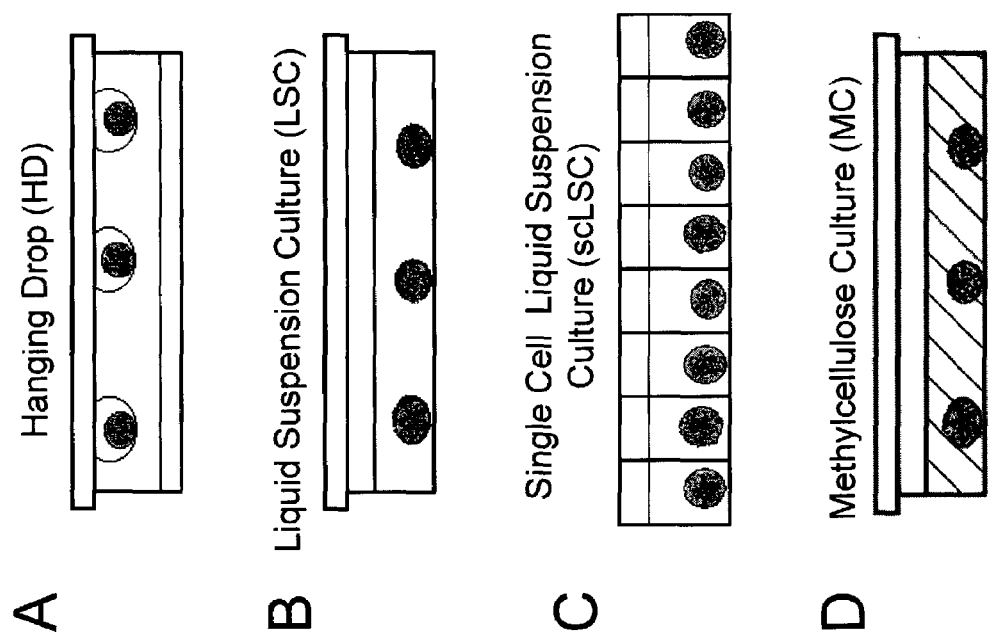
FIG. 1 is a schematic drawing of the current technologies used to culture pluripotent stem cells. (A) Hanging drop (HD) cultures typically consist of a defined number of cells allowed to aggregate in small fluid volumes that hang from the tops of tissue culture dishes. (B) Liquid suspension cultures (LSC) are typically low-density suspension cultures of individual cells or aggregates of cells. When individual ES cells are put into the bottoms of 96 well plates to measure EB developments these cultures are termed single cell liquid suspension cultures (scLSC) (C). Methycellulose (MC) (or similar solid or semi solid cultures) are cultures where cells are enveloped in semi- or semi-solid media that prevents aggregation, for example by preventing the collision of cells or cell aggregates due to its high viscosity (D).

"Adult stem cell" as used herein means an undifferentiated cell found in a tissue in an adult organism that can renew itself and can (with certain limitations) differentiate to yield specialized cell types of the tissue from which it originated or to yield specialized cell types in other tissues and organs.

"Pluripotent cell" as used herein refers to a cell that can self renew and differentiate as a cell cluster or aggregate into one or more types of cells and/or tissue. Examples of such cells include but are not limited to embryonic stem cells, embryonic germ cells, early primitive ectoderm-like cells and derivatives, multiple adult progenitor cells, adult or embryonic neural stem cells (NSC) (Toma and Akhavan, 2001; Hitoshi, Tropepe, Sibilia, et al. 1999) adult mesenchymal stem cells (MSC), mesenchymal adult pluripotent stem cells, sometimes referred to as MAPC (Schwartz, Reyes, et al. 2002), ductal stem cells (Suzuk, Zheng et al. 2002), muscle derived stem cells (McKinney-Freeman, Jackson et al. 2002).

"Embryonic stem cell" as used herein refers to pluripotent cells derived from the inner cell mass of a blastocyst, or derived by other methodologies (Jones and Thomson (2000)) and shown to be able to contribute to development of multiple tissues.

"Embryonic stem cell derived cells and tissues" as used herein refers to any cells or tissues that are derived from embryonic stem cells. The term "pluripotent cell derived cells and tissues" as used herein refers to any cells or tissues that are derived from pluripotent cells or tissues.

"Spheroid forming cell" as used herein means cells which form multi-cellular aggregates consisting of more then a single cell when cultured in suspension "Spheroid" as used herein means a cellular structure consisting of more then a single cell which has initially developed from a single or from multiple cells.

"Embryoid Body" as used herein means a "Spheroid" which is derived from embryonic stem cells.

"Clonal Spheroid" as used herein means a cellular structure consisting of more then a single cell but which has been developed from a single cell.

"Stem cell" as used herein means an "adult stem cell" or a "pluripotent cell".

"Chimeric spheroid" is a "spheroid" made up of at least two distinct cell types. For example, iinone embdoiment it has been shown that the mixing ES cells with adult pluirpotent cells can broaden the differentiation capacity of the adult pluripotent cells, for instance a chimeric spheroid can comprise two different pluripotent cell types, one an adult pluripotent cell (e.g. neuronal pluripotent cell) and the other an ES cell. In one embodiment the ES cell can induce the other cell type to differentiate into other cell types such as cardiac cells.

Description

The present invention is directed to a new method for generating spheroid-forming cell and/or pluripotent cell derived cells and tissues, such as for example cardiomyocytes, hematopoietic cells, endothelial cells, insulin producing beta cells, neuronal cells, glial cells, kidney cells, hepatocytes, vascular progenitor cells or derivatives (such as hematopoietic stem cells or endothelial cells), to name a few.

The present inventors have shown that as cell density increases, cell aggregation occurs more readily, resulting in lower cell expansion and impaired cell differentiation (also see Dang, et al. 2002). The present inventors have also hereby shown that cellular and spheroid aggregation is indeed the cause of the inability to culture spheroid-forming cells in a high density culture, such as in a liquid suspension culture (e.g. a stirred liquid bioreactor system). As such the inventors have shown that controlling cellular and/or spheroid aggregation can increase spheroid forming efficiency.

Thus in one embodiment, the invention provides a method of generating cells and/or tissues derived from spheroid forming cells, preferably pluripotent cells comprising culturing spheroid forming cells under controlled cell aggregation conditions that enable spheroid formation in liquid suspension.

In another embodiment of the method of the invention, the spheroid forming cells can be cultured under high density conditions. Although the invention will work at low cell density (even seeding the initial culture with 1 cell), it can also work with an initial cell density of about $10^2$ to about $10^6$ cells/ml, preferably about $10^3$ to about $10^6$ cells/ml, more preferably from about $10^4$ to about $10^6$ cells/ml. These cells can then be cultured under controlled aggregation conditions to yield to form spheroids. As can one start with a culture with more cells, the resulting number of spheroids formed will be greater than in cultures commenced at a lower cell density. In one embodiment, each spheroid may be cultured to about 30,000 to 35,000 cells per spheroid. It should be noted that this is but one embodiment, and the invention is not limited to such numbers. This the present method permits generation of cells at an industrial scale.

In one embodiment the invention provides a method for generating cells and./or tissues from spheroid forming and/or pluripotent cell comprising culturing the cells under conditions that control cell aggregation. In a preferred embodiment, the invention provides a method for efficient formation of spheroids or EBs and the culture of spheroid or EBs in suspension at higher cell densities. This is done by controlling cell aggregation. In one embodiment, the invention provides a scalable method for generating spheroid forming cell or pluripotent cell derived cells and tissues, such as spheroid or ES derived cells and tissues for various uses, such as for transplantation.

In another embodiment, the invention provides a method of culturing spheroid-forming cells, such as pluripotent cells in a bioreactor system where the culture conditions can be measured and controlled. In yet another embodiment, the invention provides a scalable and controllable culture of spheroid-forming cells, such as pluripotent cells by allowing them to be cultured in stirred bioreactors, such as stirred liquid bioreactors. This is done by controlling cell aggregation. This improves the efficiency of generation of differentiated cells.

In one embodiment, the bioreactor or culture system used in the invention is one that keeps the cells and/or spheroids in liquid suspension. In another embodiment, this culture system keeps the cells and/or spheroids in liquid suspension by stirring, but other methods or means can be used, such as by agitation of the system, use of various media or other environmental conditions.

The term "controlling cell aggregation" refers to the process of effectively modulating the extent and kinetics of cell aggregation such that an endpoint, not effectively attainable without such control, is achieved. As used herein in relation to cell and/or spheroid or EB aggregation, "controlling cell aggregation" means that cell aggregation can be permitted or prevented as desired. For example, in one aspect of the invention, aggregation of spheroid forming cells, such as ES cells sufficient to induce spheroid or EB formation is permitted, and aggregation between cells within a spheroid or EB is permitted. However aggregation between spheroid-forming cells or ES cells beyond that determined to induce spheroid or EB formation is prevented. Aggregation between separate EBs is also prevented.

Further, benefits of the invention (i.e. increasing efficiency of ES or pluripotent cell derived cells or tissue) can be obtained with any degree of prevention of inhibition of cellular aggregation. Controlling aggregation may, in some application consist of preventing aggregation where the term "preventing" includes any inhibition of (i.e. that may prevent some, but not necessarily all) of spheroid forming cell or pluripotent cell and/or spheroid or EB aggregation in a particular culture system. It would be appreciated by those skilled in the art upon reading the description herein that any prevention of spheroid, EB and/or spheroid-forming cell or pluripotent cell aggregation would improve cell yields in the culture system and/or cellular differentiation.

In one embodimeint, "preventing, spheroid and/or ES cell and/or spheroid or EB aggregation" means that after spheroid-forming cells or ES cells are cultured to form spheroids or embryoid bodies, there may be cellular aggregation between cells within a spheroid or embryoid body but not between cells of different spheroids or embryoid bodies or between spheroid or embryoid body themselves.

The term "embryonic stem cell derived cells and tissues" as used herein refers to any cells or tissues that are derived from embryonic stem cells. The term "pluripotent cell derived cells and tissues" as used herein refers to any cells or tissues that are derived from pluripotent cells or tissues.

Thus in one embodiment, the invention provides a method of culturing spheroid-forming cells or ES cells comprising culturing the cells under conditions that promote spheroid or EB formation, including controlled aggregation of spheroid-forming or ES cells, then preventing cell and spheroid or EB aggregation.

In another embodiment, the invention provide a method of controlling the production of spheroids from spheroid-forming cells by controlling the aggegation of such cells. In one embodiment, the spheroid forming cells are pluripotent cells such as neural stem cells which form neurospheres, or are embryonic stem cell which form EBs.

In a preferred embodiment the method of the invention does not adversely affect spheroid or EB formation, cell growth, or cell differentiation. Thus in another preferred embodiment, the method does not adversely effect the delivery of nutrients, oxygen, or cytokines. In yet another embodiment, the cells can further comprise culturing the ES cells under conditions that promote differentiation of the cells and spheroid or EB formation. In another embodiment, the cells can be cultured under conditions that does not promote cell differentiation or further differentiation. Thus the method of the invention, by adujusting culture conditions and generate differentiated cells or be used to expand the existing cell culture initially or at any point of the method. For instance, in one embodiment culture conditions can change be changed during the method to control differentiation conditions.

Examples of culturing conditions that promote spheroid forming cell or ES cell differentiation and spheroid or EB formation include but are not limited to conditions described in Keller et al. 1995 or O'Shea et al. 1999 or those outlined in Tables 10 or 11 and references noted therein to enhance generation of particular cell types. The spheroid-forming cell and other cells used in the invention can be genetically modified cells. The genetic modification can be for a variety of purposes including, to enhance cell selection by conferring particular identifying characteristic to the desired cell, to generate cells for gene or cell therapy. Other applications would be apparent to those skilled in the art.

Particular cell types can be selected for and/or harvested using a variety of methods, including cell surface receptors or other labeling, tagging or monitoring or selection methods known in the art.

Examples of conditions that can be used in the present invention for culturing spheroid-forming cells, such as ES cells to control spheroid or EB and/or cell aggregation include but are not limited to:

(a) Methods for preventing physical association between cell aggregation molecules (i.e. encapsulation, such as described herein or Sefton et al. 1997).
(b) Methods that use reduced inorganic salt concentration as described in Boraston et al. 1992 and Ko et al. 2001.
(c) Methods that block surface aggregation molecules with specific peptides or other molecules, such as described in Burdsal et al. 1993
(d) Using genetically modified spheroid forming or ES cells such as E-cadherin-null ES cells such as described in Larue et al. 1996 or methods that inhibit E-cadherin expression or antagonize or inhibit E-cadherin activity.
(e) Addition of agents that prevent cell aggregation such as dextran sulfate or other sulfated polyanions as described in Dee et al. 1997
(f) Methods that prevent cell aggregation by physically separating one ore more spheroid forming cells to enable spheroid formation in distinct compartments such as described in the single cell liquid suspension culture (scLSC) method in this patent without limitation to a single cell.

In one embodiment of the invention, the above methods can be used alone or in combination, ie. more than one method can be used to prevent spheroid, EB and/or spheroid-forming or ES cell and/or non-clonal spheroid-forming or non-clonal ES cell aggregation.

The selected spheroid forming or ES cell culturing strategy preferably does not affect the development and differentiation of pluripotent cells, preferably ES cells, or EBs in any adverse way.

In a preferred method of the invention, the spheroid-forming or ES cells are encapsulated. In one embodiment, the average number of cells encapsulated can be predetermined or conditions can be adjusted to get a desired number of cells per capsule. For instance, in one embodiment, the number of cells per capsule is 1-10, 1-5, 5, or 1, but the invention is not limited by such examples. The spheroid-forming or ES cell can be encapsulated using methods such as described in Weaver et al. 1988 or Turcanu et al. 2001 and then cultured under conditions that promote sperhoid or EB formation and cellular differentiation, such as described in Keller et al, 1995 or O'Shea et al. 1999.

A variety of methods can be used to encapsulate cells. Although, the Examples described herein use the Gel Microdrop Technique (GMD), patented and owned by One Cell Systems, Boston Mass. The GMD technique was designed to encapsulate cells in agarose gel for the purpose of isolating individual cells with specific protein secretion profiles; however, the present invention adapted the process for encapsulation of spehroid-forming or ES cells and controlling cell and spheroid or EB aggregation. It is important to note that the microencapsulation of spheroid-forming cells such as ES cells for the purposes of the present invention does not depend upon the GMD technique as any method of encapsulation could be used.

In one embodiment the size of the capsule can be controlled, for instance by tempurature, impeller spped or encapsulation time. Preferably the size of the capsule is such that maintains the spheroid-forming cells and/or sperhoids in the capsule until aggregation cell surface markers are no longer expressed. For instance, for ES cells, EBs that emerge after about 4 days no longer express E-cadherin and thus do not have a tendency to aggregate.

The matrix of the capsule can be composed of a variety of substances. Inone embodiment it is an agarose capsule. In another embodiment, the matrix should be biocompatible in that it should not have a detrimental effect on cell proliferation and/differention as desired. In yet another embodiment, the matrix should such that permits the passage or exposure of desired media components to the spheroid-forming cells or spheroid. This can be done by keeping certain components in the capsule and others out or by permitting the passage of certain components through the capsule matrix.

The conditions under which the ES cells are cultured for differentiation will depend on the type of ES cell derived cells and tissues desired. For instance, to obtain hematopoietic stem cells one would preferably culture the ES cells under certain conditions, such as described in Wiles and Johansson 1999; Rathjen et al. 1998; or Keller et al, 1993. On the other hand, if one wishes to obtain cardiomyocytes, the cells would be cultured under specific conditions, such as in the presence of specific cytokines, i.e. TGF-$\beta$ (Dickson et al. 1993), or using a selectable genetic marker such as described for cardiac myocytes in Klug et al (1996). In vitro, ES cells have been shown to differentiate into a variety of cell types and tissues, including beta cells, cardiomyocytes, hepatic cells, kidney cells, neuronal cells, and hematopoietic cells. Various cell types and culturing conditions are described in Zandstra and Nagy, 2001 for general approaches; Wang et al, 1992 for endothelial cells; Rohwedel et al., 1994, Fleishman et al, 1998 and Mummery et al. 2002 for cardiac and muscle cells; Bain et al, 1995, Tropepe et al, 1999 and Reubinoff et al. 2001 for neuronal cells; Palacios et al, 1995 and Kyba et al., 2002 for hematopoietic stem cells; Choi et al, 1998 and Levenberg et al. 2002 for hematopoietic and endothelial cells. Assady et al 2001 for insulin-producing cells. Since the differentiation of the ES cells results in a complex mixture of all possible cell types an efficient enrichment protocol would be necessary to obtain a homogeneous population of specific cell types or tissues to be utilized for various purposes including the generation of surrogate cells for human therapies or for drug screen testing. This enrichment could be done by the introduction of a specific construct into ES cells, comprising a cell or tissue type specific promoter controlling the expression of a marker gene. The resulting transgenic ES cell(s) can be expanded, differentiated and selected to generate the desired cell type of interest using techniques known in the art, for instance as described in Klug et al (1996) for cardiac cells (WO 95/14079, May 26, 1995; U.S. Pat. Nos. 5,733,727 and 6,015,671) or Soria et al (2000) or Soria et al (2001). The method is widely applicable to any cell type for which the tissue specific promoter is known. Table 9 provides some examples of promoters useful for the selection of specific cell lineages without limiting the number of useful promoters to that table.

The initial undifferentiated spheroid-forming or ES cells used in the method can be obtained by methods known in the art. For instance one can use ES cells obtained directly from the inner cell mass of the embryo, or one can use ES cells that were cultured, i.e. expanded under conditions that did not promote differentiation, such as described in Klug et al. 1996.

The encapsulation material chosen should prevent aggregation of cells contained in different capsules. Suitable material would include but is not limited to agarose, alginate, polymers such as poly HEMMA (Valbacka et al (2001) and others or matrices described in Weaver et al. (1988) and Sefton et al (1977).

The material selected for encapsulation should permit adequate delivery of any desired nutrients, cell culture media, growth factors, cytokines, or any other factors to promote desired ES cell growth, differentiation and EB formation, e.g., through functionalization of the encapsulation matrix, or by diffusion through the pores. The material selected may depend on the factors that are to be delivered. Example of matrices that could be used are agarose, alginate, and polymers that support cell growth. Examples of suitable matrices are described in Weaver et al. (1988) and Sefton et al (1977). However, a person skilled in the art would be familiar with other suitable matrices. In another embodiment of the invention, the size of the capsule can be controlled, which can determine the time at which the EB emerges from this capsule. In one approach, varying the rate of emulsification during the encapsulation process can control the size of the microcapsule. The different capsule sizes produced under each of the conditions tested are shown in Table 3. Other factors that may control the size of the microcapsules include the addition of surfactants to the encapsulation solution, the ratio of encapsulation gel to liquid, and others factors that would be familiar to those practiced in the art upon reading this description. The efficiency of cell production could be affected by the timing of the emerging EB, as once the EB emerges from the capsule, that particular method of prevention of EB aggregation would be gone. The effect of any subsequent EB aggregation would depend on the stage of development of the emerged EB and any limitations in size (numbers of cells) of an EB. The size of the capsule could also effect efficiency of delivery of various growth or differentiation factors or any other factors or nutrients to the cells. For instance larger capsules would have greater surface in which such factors could pass through, or provide a substrate onto which one could functionalize bioactive molecules (Irvine et al, 1998). This could also be accomplished by controlling the porosity of the encapsulation matrix. In one embodiment, the method of the invention enables the culture of differentiating ES cells in conventional commercially available bioreactor systems that include the use of standard bioprocess equipment (probes, filters, etc).

In another embodiment the method of the invention enables culture of differentiating spheroid-forming or ES cells in stirred 3-dimensional reactors with scalable volume.

In yet another embodiment the invention allows for measurement and control of the culture environment by enabling the use of stirred or other well-mixed bioreactors.

As a result of being able to better control the ES cell culture environment, the method of the invention enables one to better study various conditions to obtain particular differentiated ES cells and tissue (i.e. hematopoietic cells, cardiomyocytes, nerve cells, beta cells, hepatic cells, kidney cells, any other cell types differentiated or not, known to develop from embryonic stem cells) and to better optimize these conditions. As such, the method of the invention can be used to derive a cell culture with a higher density of desired differentiated cells. The ability to do this may determine whether or not the process is economically viable and therefore is critical to the translation of these technologies from the lab scale. The method of the invention can also be used to identify factors (e.g., any variant, such as growth factors, differentiating factors, such as cytokines, or other conditions, such as pH, temperature, oxygen or factor concentration levels) and conditions that effect and preferably optimize spheroid froming cell or ES cell differentiation and spheroid or EB formation. Examples of some factors, especially for studying spheroid forming cell or ES cell differentiation to cardiomyocytes include but are not limited to fibroblast growth factors (FGFs), vascular endothelial growth factor (VEGF), cardiotrophin-1 (CT-1), leukemia inhibitory factor (LIF), endothelin-1(ET-1), stem cell factor (SF), opiod peptide (or supplemental DMSO), bone morphogenic protein (BMP) family members transforming growth factor beta (TGF-beta), retinoic acid (RA). Factors preferably used to study beta-cell differentiation include but are not limited to, glucose levels, nicotinamide, KGF (karatinocyte growth factor), EGF (epithelial growth factor, NGF (neural growth factor) and TGF-beta, the above factors, as well as others typically used on adult hematopoietic stem cells (Zandstra et al 1997) can also be used to elicit the development of hematopoietic and endothelial cells from pluripotent cells. This method would comprise culturing the spheroid forming cells or ES cells under conditions that control cell aggregation in the presence of the particular factor to be tested and then detecting the effect of the variant on cell proliferation and differentiation. Preferably a negative control is used, whereby the spehroid-forming cells or ES cells are cultured in the absence of the factor to be tested.

The methods and products of the invention can also be used to produce cells for drug therapy testing, to identify targets for gene and cell therapy, and in assays for such methods.

ES cells and the ES cell derived cells and tissues can also be used in the treatment of various cancers, leukemias, autoimmune diseases, organ failure, animal or tissue cloning, gene therapy, transgenic animals.

The ES cell-derived cells and tissues obtained from the invention can be used to provide cells and tissues for transplantation. For instance, ES cells can be grown under conditions to produce hematopoietic cells. Such cells could be used in bone marrow transplants, blood transfusions or infusions. ES cell derived cardiomyocytes can be used in tissue engineering, cell/tissue transplantation, gene therapy, and drug discovery. ES cells derived skin tissue can be used for reconstructive surgery, ie. for burn victims, cosmetic surgery to name a few.

Further examples of applications for ES derived cells and tissues can be found in Rathjen et al 1998 or Marshall E. 2000.

It should be noted that although the discussion above describes the invention in terms of ES cells, the same methods and applications and products of the invention would be applicable to pluripotent cells in general or spheroid forming cells other than ES cells.

In a further embodiment, the invention provides a method for the selection of specific cell types from spheroid forming cells comprising the steps of:

i. introducing a reporter gene expressing vector into at least one spheroid forming cell whereby a cell-type specific promoter is combined with an reporter gene, such that the reporter gene is expressed under the control of the cell-type specific promoter;

ii. culturing the spheroid forming cell(s) comprising the method of claim 1 iii. differentiating spheroid forming cell(s)

iv. isolating and harvesting the specific cell-type based on the reporter gene expression In one embodiment, the reporter gene is an antibiotic resistance gene and the cell-type of interest is isolated by the addition of an appropriate antibiotic in step (iii) or (iv).

In yet another embodiment, the method for the selection according to the reporter gene is selected from the group consisting of the Hygro mycin resistance gene (hph), the Zeocin resistence gene (Sh ble), the Puromycin resistance gene (pacA), and the Gentamycin of G418 resistance gene (aph).

In yet another embodiment, in the method for the selection according to claim 23, wherein the reporter gene is selected from the group consisting of luciferase, green fluorescence protein, red fluorescence protein, and yellow fluorescence protein and the cells of interest are selected by fluorencent activated cell sorting (FACS).

In yet another embodiment, in the method for the selection according to the reporter gene is selected from the group consisting of luciferase, green fluorescence protein, red fluorescence protein, yellow fluorescence protein, or a his-, myc-, or flag-tag ligated to a heterologous gene, or any heterologous gene which when expressed is inserted into the cellsurface and the cells of interest is isolated from the cultured cells by affinity purification.

In yet another embodiment, in the method for the the cell type specific promoter is selected from those listed in Table 9 for cell types listed therein.

The present invention also includes the Embryonic stem cell derived cell culture obtained using the method of the invention.

In yet another embodiment the invention is directed to a method to identify factors that effect cell proliferation, differentiation and/or spheroid formation, said method comprising culturing the cells as per the method of the invention in the presence of the factor to be tested and then monitoring the effect of the factor on cell proliferation, differentiation and/or spheroid formation.

In another aspect, the invention provides a method of generating cells derived from spheroid forming cells in accordance with claim 1 wherein the spheroid forming cells are cultured under conditions that enable spheroid formation, said conditions comprising culturing said spheroid forming cells in liquid suspension under non-aggregating conditions.

In another aspect the invention provides a culture bioreactor for industrial production of cells derived from spheroid forming cells comprising:

a. culturing spheroid forming cells in accordance with the method of claim 1, wherein the cells are cultured in a spheroid forming cell suitable media under conditions that promote spheroid formation; while b. Inhibiting spheroid aggregation.

In another embodiment the invention provides a method to prevent aggregation between cells comprising encapsulating a cell or group of cells and thus preventing aggregation of said cells with cells not within said capsule.

In another embodiment, the invention provides a bioreactor for generating cells from spheroid forming cells comprising a means for controlling conditions suitable for spheroid formation, such conditions comprising a means for controlling cellular aggregation and means for maintaining said cells and generated cells in suspension, such as means for preventing cellular aggregation.

Further the invention also encompassed the use of encapsulating cells, as described herein to control the micro environment of a cell to be cultured. This is not limited to spheroid-forming or ES cells.

The following non-limiting examples are illustrative of the present invention:

EXAMPLES

Materials and Methods

ES Cell Culture

Murine embryonic stem cells: CCE, R1, D3 (mentioned below) and others (Beddington and Robertson, 1989; Nagy, Rossant et al., 1993), were maintained at 37° C. in humidified air with 5% $CO_2$ in Iscoves Modified Dulbecco's Medium (IMDM, GIBCO-BRL) supplemented with 15% fetal bovine serum (Hyclone), 50 U/ml penicillin (GIBCO-BRL), 50 µg streptomycin (GIBCO-BRL), 2 mM L-glutamine (GIBCO-BRL), 0.1 mM 2-mercaptoethanol, and 500 pM leukemia inhibitory factor (LIF) (ES cell media). Culture flasks were prepared prior to cell seeding by coating with a solution of 0.1% porcine gelatin in phosphate buffered saline. All ES cells were used between passages 15-24.

ES Cell Differentiation Systems

ES cells were dissociated using 0.25% trypsin-EDTA (Sigma) and cultured in ES cell medium without LIF to induce differentiation. Liquid suspension cultures (LSC) were prepared by aliquoting 10 ml of cell solution at the indicated ES cell density into 10 cm petri-dishes (Fisher). For single ES cell analysis (single cell liquid suspension culture scLSC), a single ES cell was placed into each well of a 96 well plate (Nunc) coated with 10% pluronic (F-127, Sigma) solution to prevent cell attachment. This was achieved by preparing a suspension of 20 ES cells/ml and aliquoting 50 µL into each well. Each well was then visually inspected for the actual number of deposited cells. Empty wells or wells with more than one cell were marked and not included in the analysis. Methylcellulose cultures (MC) were prepared by aliquoting 1 ml of cell suspension with 1% methylcellulose (M3220, Stem Cell Technologies) at the indicated ES cell density in 35 mm Greiner dishes (Greiner Labortechnik). Hanging drop cultures (HD) were prepared using 10 µL droplets, each containing the number of ES cells desired to initiate the EB (as indicated). ES cells were allowed to aggregate in hanging drops for two days before transfer to liquid suspension culture.

Stirred cultures were performed in spinner cultures (Bellco Glass) ranging from 50 to 250 ml of media/vessel. ES cells were added to the media directly (stirred cultures without encapsulation: SC) or encapsulated (ESC) as indicated. A paddle-style impeller was used to agitate the media at 40-60 RPM.

EBs were enumerated by visual inspection. EBs were dissociated by incubation (1 min, 37° C.) in 0.25% trypsin-EDTA (Sigma), or incubation (30 min, 37° C.) in 0.25% collagenase (Sigma) in PBS supplemented with 20% fetal bovine serum for post day 7 EBs. Mechanical shearing was also used to help dissociate cells into a single cell suspension by twice passaging the cell mixture through a 21-gauge needle and syringe (Becton Dickinson). Individual cells were then counted using a hemocytometer and analysed by either myeloid-erythroid colony-forming cell (CFC) assay (Zandstra et al. 1997) or flow cytometry (Zandstra et al. 1997)

Gel Microdrop (GMD) Encapsulation of Individual ES Cells

Individual CCE ES cells were suspended in Hanks Buffered Saline Solution (HBSS) at a concentration of $10^7$ cells/ml and added to a 3% agarose solution for a final cell concentration of $2*10^6$ cells/ml. The agarose solution was dispensed into mineral oil (nonsolvent) at 37° C. and subjected to impeller blending using the One Cell System (Ryan et al., 1995) to create agarose microdrops containing individual ES cells. The GMDs were washed twice with HBSS to remove the mineral oil before resuspension in ES cell media without LIF for differentiation culture.

Gel Microdrop(GMD) Encapsulation of Multiple ES Cells

Three different methods were used to encapsulate multiple ES cells.

(1) ES cells were gently dissociated from adhered culture using trypsin, creating multi-ES cell clumps or aggregates. Clumps were subsequently encapsulated as described for individual ES cells.

(2) ES cells were dissociated to a single cell suspension and cultured at high cell density (>$10^5$ cells/ml) in unagitated petri dishes for 12-24 hours to induce cell clump formation via controlled aggregation The average number of ES cells per clump was controlled by input cell density and by time, and was determined by dividing the input number of ES cells by the number of clumps counted ES cellclumps were then encapsulated as described.

(3) Individual ES cells were mixed with agarose at a concentration of $1-5 \times 10^7$ cells/ml and encapsulated as described. Capsules formed in this way were essentially clumps of individual ES cell held together by agarose matrix. Capsules themselves were considered ES cell clumps and again encapsulated as described.

Hematopoietic Colony Forming Cell Assay

Cells were plated into methylcellulose medium (M3434, Stem Cell Technologies) containing 50 ng/ml mrSCF, 10 ng/ml mrIL-3, 10 ng/ml hrIL-6, 3 U/ml hEpo, 15% fetal calf serum, 0.1 mM 2-mercaptoethanol, and 2 mM L-glutamine. Hematopoietic colonies were scored by morphology after 6-7 days.

Generation of Cardiac Myocytes from ES Cells

CCE and R1 embryonic stem cell were transfected with the MHC-neo$^r$/PGK-hygro$^r$ DNA as previously described (Klug et al 1996, WO 95/14079, May 26, 1995; U.S. Pat. Nos. 5,733,727 and 6,015,671). Briefly, 1 mg of DNA and 25 mg of salmon testes DNA were mixed in a total volume of 800 mL of cells suspended at $4 \times 10^6$ cells/mL on ice. Cells were electroporated (180 volts, 80 mF), incubated on ice for 15 minutes, and plated in 100 mm Corning dishes in ES media containing 500 pM LIF. Cells containing the plasmid were selected by culture in ES medium with LIF and 200 mg/mL hygromycin B for 7 days with daily medium exchange. Test ES cells were then encapsulated using the multiple ES cell encapsulation technique as described above in the third technique. After 8-10 days of culture in stirred suspension bioreactors (Bellco spinner flasks or Applikon 1 L cell culture bioreactors) in ES cell media without LIF, the G418 was added to the medium to select for the cardiac cells. The composition of the selected cells was analyzed by MF-20 staining using flow cytometry. $5 \times 10^5 - 10^6$ cells to be stained for MF-20 were washed with PBS and fixed with 100 µl of IntraPrep™ Permeabilization Reagent 1 (Immunotech, Westbrook, Me.) for 15 minutes at room temperature. After washing once with 1 ml PBS, the cells were permeabilized for 5 minutes with IntraPrep™ Permeabilization Reagent 2 and incubated with a 1:10 dilution of the mouse anti-sarcomeric myosin heavy chain (MF-20) antibody (Transduction Lab, MA) for 15 minutes at room temperature. After washing once with PBS, secondary FITC-conjugated goat anti-mouse IgG antibody was added with 1:100 dilution and the cells were incubated for 15 min at room temperature. In addition, some of the dispersed cells were used for determining the viability of the cells immediately after the procedure of enzymatic dissociation. Test cell populations were washed in ice-cold Hanks hepes-buffered salt solution containing 2% FCS (HF) and resuspended at $10^6$ cells/100 µL in HF. Finally, the cells were analyzed on a flow cytometer (XL, Beckman-Coulter, Miami, Fla.) using the EXpoADCXL4 software (Beckman-Coulter). Positive staining was defined as the emission of a level of fluorescence that exceeded levels obtained by >99.9% of cells from the control population stained with only the secondary antibody. Cardiac development was also determined by electron microscopy.

Generation of Hematopoietic and Endothelial Cells

Hematopoietic and endothelial cells were generated in through ES cell diffierentiation in ES cell media without LIF under the conditions described in Dang et al. 2002. Input ES cells were encapsulated using the multiple ES cell encapsulation technique as described above in the third technique.

Flow Cytometry for Analysis of Endothelial and Hematopoietic Cells

Cells were washed in ice cold Hanks hepes-buffered salt solution containing 2% FCS (HF) and resuspended for 10 min at 4° C. in HF containing α-mouse CD16/CD32 monoclonal antibody (PharMingen) at 1 μg/100 μL to block non-specific binding. Blocked cells were then incubated at $10^7$ cells/ml for 40 min at 4° C. with FITC anti-mouse CD34 (PharMingen), PE anti-mouse Flk1 (PharMingen), and anti-mouse E-Cadherin (Sigma). Anti-mouse E-Cadherin incubation was followed by two washes in ice cold HF and then incubated for 40 min at 4° C. with anti-mouse FITC-conjugated IgG (Sigma). Stained cells were washed twice in ice cold HF, and 1 μg/ml 7-amino-actinomycin D (7AAD, Molecular Probes) was added to the final wash. The cells were analyzed on Coulter Epics XL using 4-Colour Expo 32 software for analysis. Positive staining was defined as the emission of a level of fluorescence that exceeded levels obtained by >99.9% of the cells from the same starting population stained with a matched fluorochrome-labelled irrelevant isotype control antibody.

Measurement of Media Composition

Oxygen tension, in addition to other parameters, was measured by withdrawing 3 ml of culture media using a gastight syringe (Hamilton), and analyzing using a BioProfile 200 blood/gas analyzer (Nova Biomedical).

Neurosphere Formation

R1 murine embryonic stem cells were dissociated into a single cell suspension and transferred at $10^4$ ES cells/ml to media comprised of Dulbecco's Modified Eagle Medium (DMEM, GIBCO-BRL) supplemented with 20% Knockout serum replacement (Sigma), 50 U/ml penicillin (GIBCO-BRL), 50 mg streptomycin (GIBCO-BRL), 2 mM L-glutamine (GIBCO-BRL), and 0.1 mM 2-mercaptoethanol.

Example 1

Effects of Cell-Cell Adhesion and EB Aggregation on ES Cell Culture

To assist in the development of a new bioprocess, the properties of ES cells and EBs that might affect bioprocess efficiency, net cell expansion, and cell fate decisions were investigated. EB formation, growth and development between different culture techniques were compared. Once an understanding of these basic parameters was obtained, guidelines to the design of efficient, scalable bioprocesses were developed.

(a) Some ES Cell Lines can form EBs from Individual Cells.

Preliminary studies focused on establishing the in vitro developmental potential of individual ES cells. In single cell liquid suspension (scLSC) and methylcellulose culture (MC), EB efficiency (number of EBs divided by input number of ES cells) have been reported anywhere between 2-15%. Because these values were so low, it was uncertain as to whether an individual ES cell could form an EB, or if EB formation occurred only when ES cells aggregated by chance (or by design, as in the hanging drop method). Therefore the first constraint investigated was the number of ES cells required to form an EB.

Individual murine CCE ES cells were placed by limiting dilution into separate wells of a 96 well plate and differentiated in liquid suspension culture (ES media without LIF). One hour after plating, each well was visually examined to verify the number of cells plated. After seven days of differentiation, the wells were examined for cell aggregates. The cell aggregates were identified as EBs based on their expression of Flk-1 and CD34, and their ability to form hematopoietic colonies (data not shown). By dividing the total number of EBs per 96 well plate by the number of input ES cells, we determined that individual ES cells were able to form EBs with an overall efficiency of at least 42±9% (Table 1). In a separate set of experiments, it was determined that 78±9% of the starting cell population were undifferentiated ES cells based on E-cadherin and SSEA-1 expression (data not shown, (Zandstra, et al. 2000)). Viability, based on exclusion of dead cell dye 7AAD, of the ES cell population after trypsinization was determined to be 87±11%. This allowed recalculation of the EB formation efficiency from individual, undifferentiated, and viable ES cells to be approximately 60%. These results clearly demonstrated that a majority of individual murine CCE ES cells have the capacity to form an EB, and that these cells could form EBs at a very high efficiency. However, the results also raise the issue of why such high efficiencies were not regularly achieved in standard differentiation cultures.

The present inventors have shown that murine CCE ES cells have demonstrated the ability to form EBs from single ES cells. In other cell types or under other conditions contact between multiple ES cells to enable EB formation may be preferred. For example, the present study repeated with single murine R1 and D3 ES cells did not form single ES cell derived EBs under the conditions used Instead, aggregation with approximately 5 or more ES cells was required for survival, proliferation and differentiation (see below). Similarly, it has been reported [Thomson J A, Odorico J S. 2000] that current human ES cell lines form EBs only from multi-ES cell aggregates or clumps. Regardless, the following aggregation studies reported with CCE ES cells are still illustrative of the extent of EB aggregation and the problem it poses. As such controlling cellular aggregation during expansion and differentiation of said cells is an important factor.

(b) EBs Aggregate, Reducing EB Formation Efficiency

Figure 3:
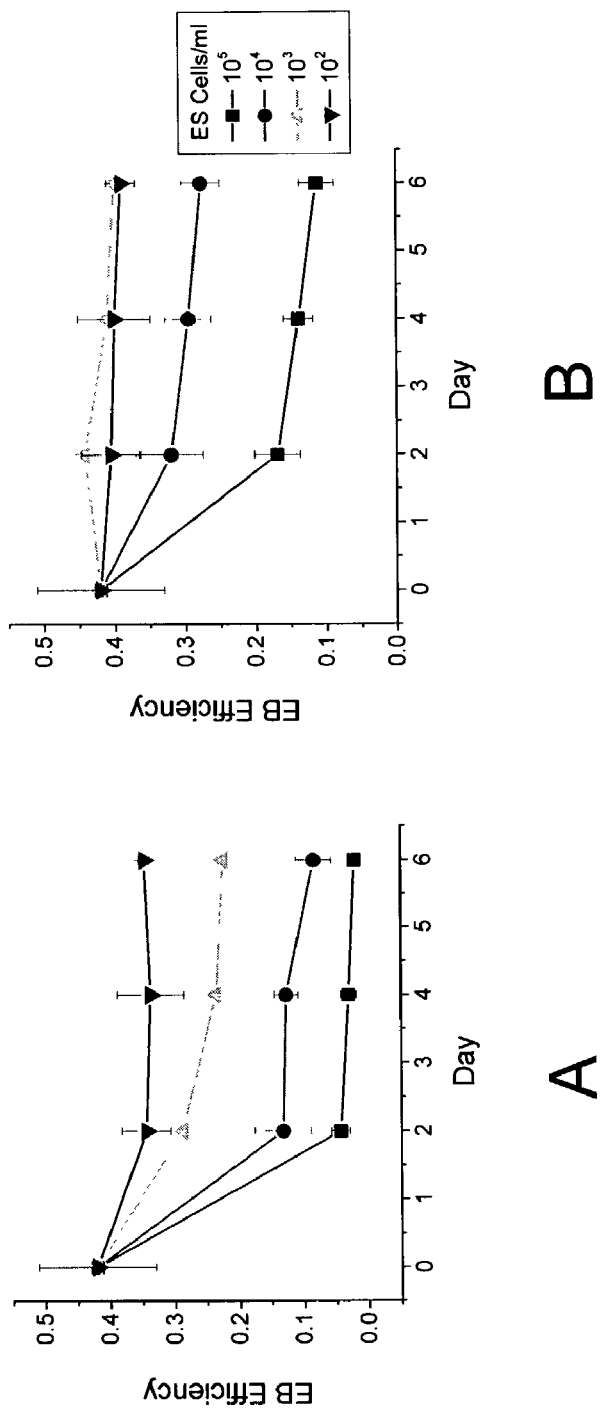
FIG. 3 is a graph illustrating the affect of initial ES cell density (i.e., number of ES cells per unit volume) on EB efficiency (ratio of number of cell aggregates to number of input ES cells) over time for A: liquid suspension culture (LSC) and B: methylcellulose (MC) culture. Cultures were initiated with ES cell densities: $10^2$, $10^3$, $10^4$, $10^5$ cells/ml.

Further investigation revealed the sensitivity of EB efficiency to initial ES cell concentration and time (FIG. 3). Various initial CCE ES cell concentrations were differentiated in liquid suspension and methylcellulose cultures, and the number of cell aggregates (EBs) per dish was recorded at regular time intervals. In liquid suspension culture, EB formation efficiency increased as ES cell concentration decreased (FIG. 3A). Over time, EB formation efficiency decreased for all cell concentrations. However the extent of this decrease was most dramatic in cultures initiated with $10^5$ ES cells/ml, and almost nonexistent at $10^2$ ES cells/ml. In methycellulose cultures (FIG. 3B) initiated with $10^3$ ES cells/ml or less, EB formation efficiency remained constant at approximately 40% over the duration of the experiment. EB formation efficiency gradually decreased in methylcellulose cultures initiated with $10^4$ or more ES cells/ml, however to a lesser extent than their liquid suspension counterparts.

Based on their similarity, the model of the present invention for EB formation from single ES cells (42±9%) was reconciled with EB efficiency in methylcellulose culture initiated with $10^3$ ES cells/ml or less (40%±6%) and liquid suspension culture initiated with $10^2$ ES cells/ml or less (34±5%). However, an explanation was still required for the discrepancy with the results obtained at higher cell concentrations. It was recognized that the decrease in EB efficiency over time indicated that the process of EB formation itself was unaffected; rather, another process occurring post-EB formation must be reducing the number of EBs present. Observing the cultures, it was apparent that EB aggregation was the cause of inefficiency. In this process, separate EBs aggregated and merged into a single, larger EB.

This phenomenon accounts for decreased EB efficiency with increased cell concentration since likelihood of EB collision and subsequent aggregation would also be greater. Furthermore, aggregation explains the higher EB efficiency in methylcellulose cultures compared to liquid suspension culture: Semi-solid methycellulose media impaired cell movement, thereby decreasing likelihood of EB collision and aggregation.

(c) Aggregation Reduces Net Cell Expansion

Figure 4:
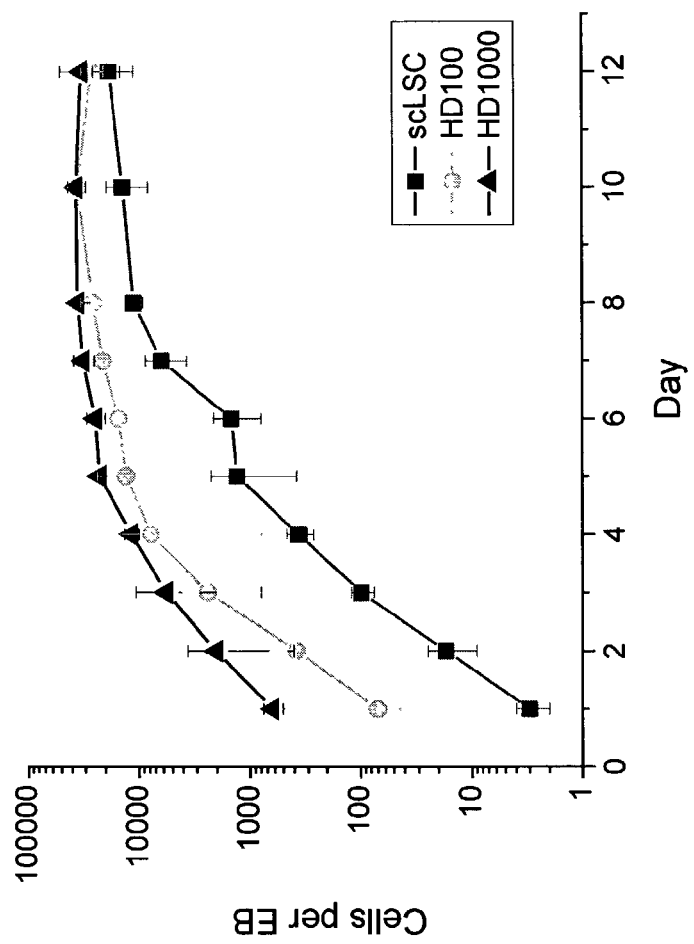
FIG. 4 is a linear graph illustrating cells per EB (y-axis) over time (x-axis). EBs were initiated with: 1 (scLSC), 100 (100 cells per drop in the hanging drop cultures, HD100), and 1000 (1000 cells per drop in the hanging drop cultures, HD1000) ES cells/EB. Despite initial differences in cells/EB, all EBs grew to approximately the same size by day 12.

The results demonstrate that CCE ES cells form EBs with an efficiency of 42±9%, a value independent of culture method and initial ES cell concentration, and that EB aggregation reduced the apparent efficiency over time. To determine what effect EB aggregation might have on the overall production of cells, the growth rate of various initial ES cell aggregate sizes (1, 100, and 1000 ES cells/EB) formed using the single cell liquid suspension culture (scLSC) and hanging drop techniques were compared (FIG. 4, Table 2). Regardless of initial aggregate size, all EBs contained a similar number of cells by day 12. Since final EB size is independent of EB aggregation, EB aggregation reduces overall expansion of cells.

(d) Cell-Cell Adhesion Molecules are Responsible for EB Aggregation

Figure 5:
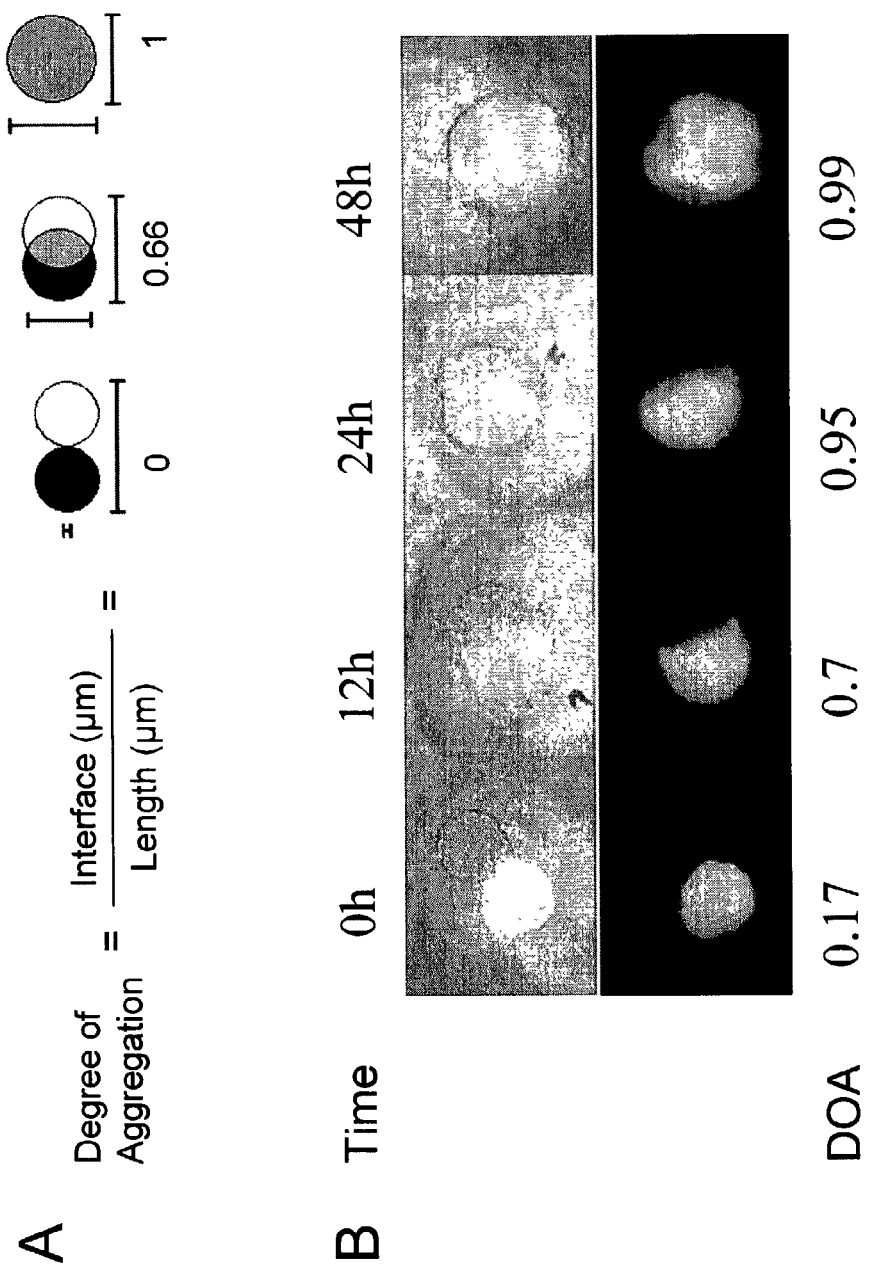
FIG. 5(A) illustrates the method of quantifying degree of aggregation (DOA) between two EBs, defined as the ratio of the diameter of the interface to the overall length of the two EB system. DOA is calculated by dividing the interface diameter by the overall length of the two EB system, yielding a scale between 0 (no aggregation) and 1 (fully aggregated). (B) A representative photomicrograph series of two EBs aggregating over time is shown with corresponding DOA measurements at each time interval. Two types of ES cell derived EBs were used in this experiment, one that was not fluorescent and one that was constitutively fluorescent (light EB in the photomicrograph)).

The process of EB aggregation was studied using the simplest scenario: aggregation of two EBs. To visualize cell mixing, one EB generated from wildtype ES cells was aggregated with one EB generated from ES cells constitutively expressing GFP (Hadjantonakis et al 1998)). The extent of aggregation was quantitatively determined by the "degree of aggregation" (DOA)—the ratio of the diameter of the interface to the overall length of the two EB system (FIG. 5). Regardless of initial aggregate size (50, 100, 400 ES cells/EB, data not shown), complete fusion (DOA>90%) was achieved after approximately 16 hours and complete cell mixing (homogenous fluorescence intensity) after 48 hours (FIG. 5).

Figure 6:
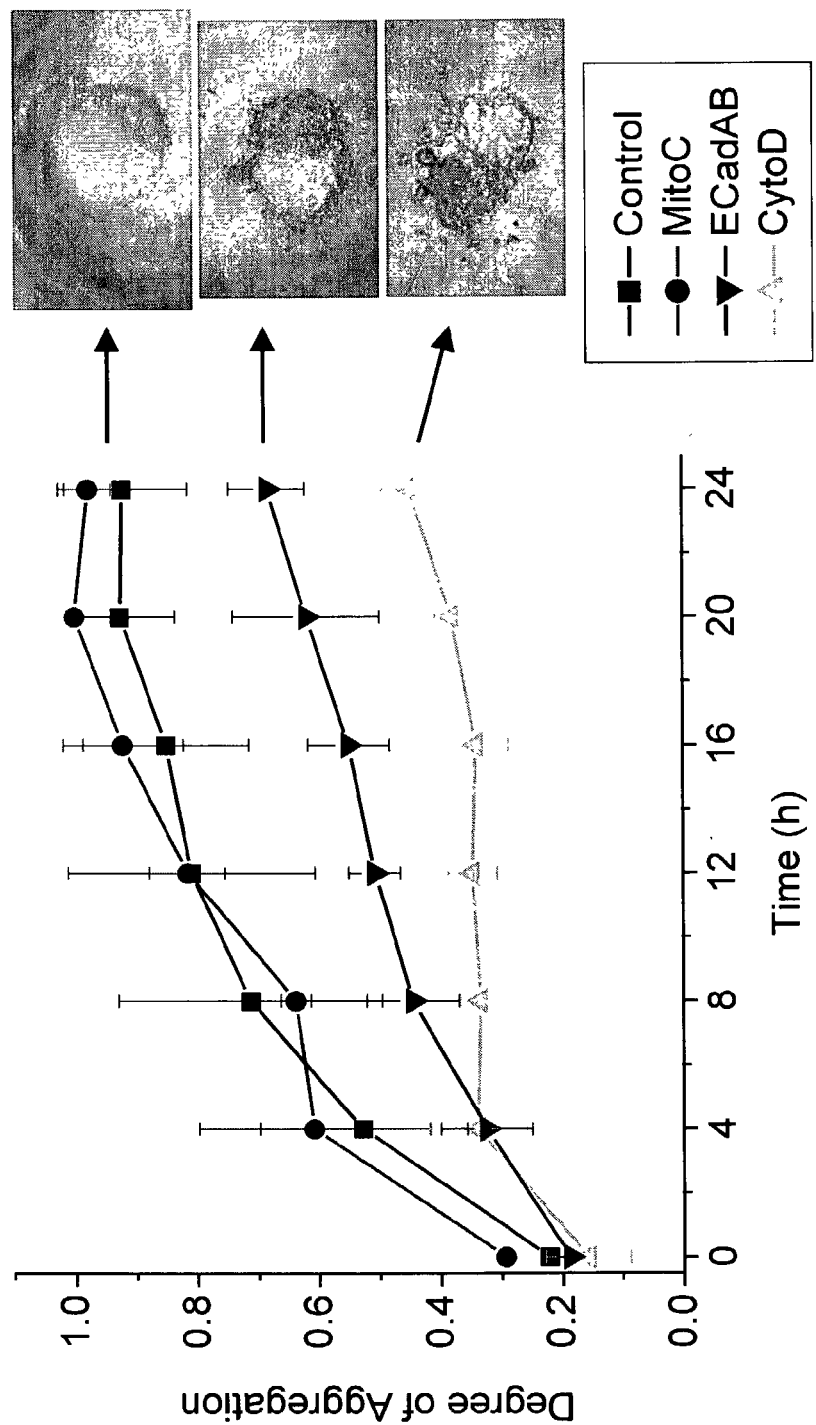
FIG. 6 is a linear graph illustrating the effects of the chemical additives cytochalasin D (CytoD), mitomycin C (MitoC), E-cadherin blocking peptide (ECadAB), and a control, on the aggregation kinetics, measure using the DOA, of EBs. A representative photo taken at 24 hours of culture is shown for each treatment group.

The mechanism of EB aggregation was investigated using various loss of function treatments (FIG. 6). Blocking surface cell adhesion molecules with blocking peptide inhibited EB aggregation. E-cadherin blocking was particularly efficient, also noted by Larue et al. (1996) who observed that homozygous E-cadherin null ES cells were unable to aggregate as clumps. EBs treated with cytochalasin D also were unable to aggregate. Cytochalasin D inhibits actin-dependent processes including cell migration and cell division. To be sure that impaired cell division was not responsible for this effect, another group was treated with Mitomycin C that inhibited mitosis by preventing DNA synthesis. These EBs aggregated at the same rate as the control (no treatment). Based on these results, a two-step mechanism for EB aggregation was proposed: First, neighboring EBs collide and homophilic E-cadherin molecules adhere, holding the EBs together. Cells then migrate and remodel as the EBs fuse into a single spheroid.

Figure 7:
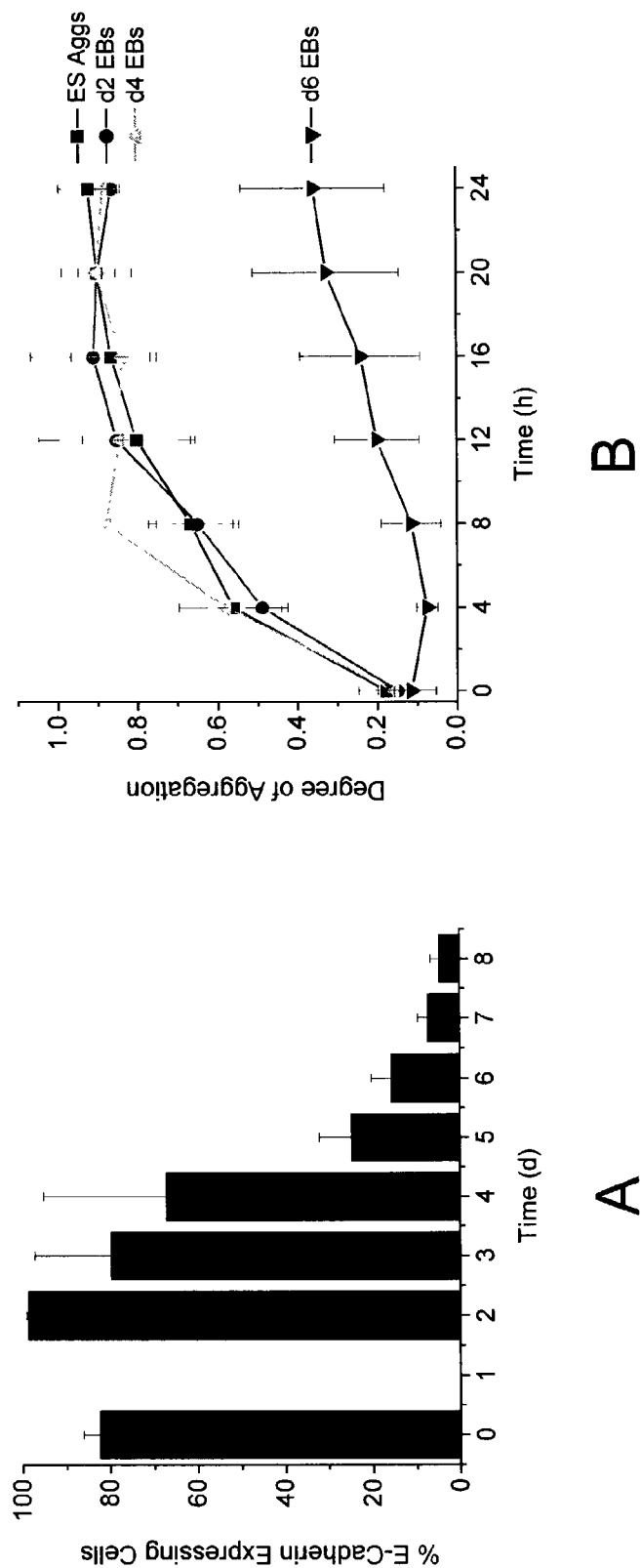
FIG. 7 panel A is a bar graph illustrating percent E-cadherin expressing cells (y-axis) versus time (x-axis).

Preventing cell adhesion versus cell migration between neighboring EBs was the logical strategy for preventing EB aggregation as treatments that could affect cell growth or differentiation (i.e. cytochalasin D) would be undesirable for most applications. E-cadherin, the prominent cell adhesion molecule in this process, is a $Ca^{2+}$-dependent homophylic cell-cell adhesion molecule expressed by ES cells. As ES cells differentiate, E-cadherin expression is downregulated (Zandstra et al. 2000). Using flow cytometry, E-cadherin expression was tracked in differentiating EBs over time (FIG. 7.A). Expression decreased as cells differentiated—from almost 100% on day 0 (ES cells) to approximately 25% by day 5 of differentiation. As expected, E-cadherin expression correlated with rate of EB aggregation: EBs differentiated for four days or fewer aggregated within 16 hours, while day 6 EBs did not aggregate (FIG. 7.B). Similarly, while ES cells placed into stirred culture quickly aggregated into large cell clumps that did not grow or differentiate properly, EBs grown in static culture for a minimum of four days could be transferred to stirred culture with little aggregation. These EBs continued to grow and differentiate normally. Therefore, the strategy adopted for controlling cell adhesion need only be implemented while cell adhesion molecule expression remains high. For murine ES cells, this time period is the first four days of differentiation.

These results suggest that novel approaches to control the aggregation of undifferentiated ES cells and their derivatives may allow them to be cultured in high cell density, stirred suspension bioreactors.

Example 2

Figure 2:
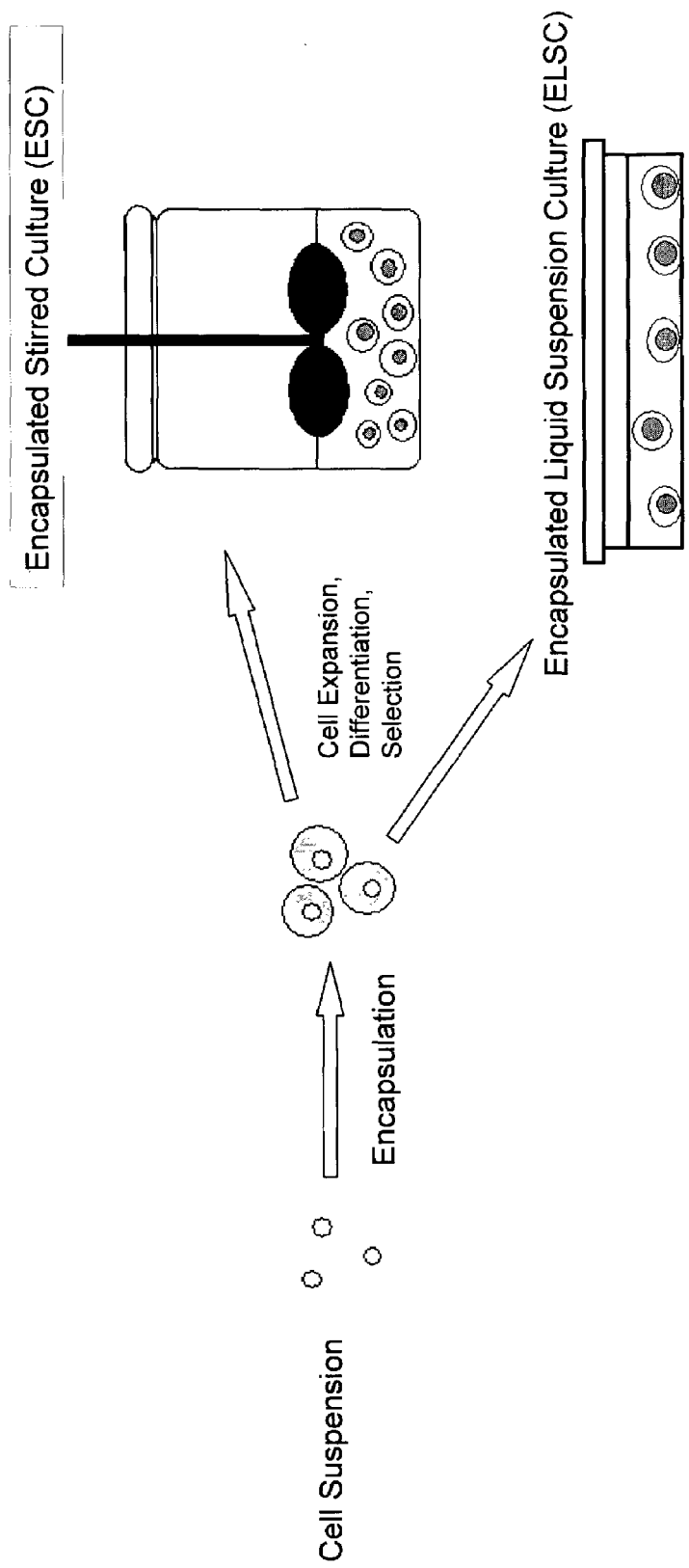
FIG. 2 is a schematic diagram of one embodiment of the method to control spheroid forming cell and/or plurioptent cell and spheroid aggregation. Test cell populations (either individual cells or controlled aggregates of cells) are encapsulated, put inside a controlled stirred suspension bioreactor (Encapsulated Stirred Culture (ESC)), or in any type of encapsulated liquid suspension culture (ELSC) where, because of the encapsulation technology, they are prevented from aggregating, and allowed to proliferate and differentiate into the desired cell type.

Preventing ES Cell-Cell Adhesion and EB Aggregation Results in Efficient Generation of Embryonic Stem Cell Derived Hematopoietic and Endothelial Cells The overall schematic of one embodiment of the bioprocess of the invention for the scalable culture of ES cell derived tissues is shown in FIG. 2. First, undifferentiated ES cells are expanded under appropriate conditions. ES cells are then cultured in a bioreactor conditions that control aggregation and promote cell proliferation and differentiation. More specifically, aggregation of ES cells to induce EB formation is permitted and aggregation between cells within an EB is permitted. However aggregation between ES cells beyond that required to induce EB formation is prevented, and aggregation between separate EBs is prevented.

After an appropriate period of culture, under defined conditions (including growth factor and medium formulation, oxygen tension, pH, medium supplementation rates), differentiated cells are selected for and used in clinical or pharmaceutical applications. In one aspect, the present invention is primarily concerned the scalable generation of ES cell derived cells and tissues.

(a) Culture of EB Under Non-Aggregating Conditions

Genetically Modified ES Cells

E-cadherin$^{-/-}$ ES cells are defective in cell adhesion, unable to grow as clumps or aggregates of cells as they typically do (Larue, Antos et al. 1996).

Antibodies to Block Cell Adhesion Molecules

As reported in the present study of EB aggregation, treatment of EBs with E-cadherin blocking peptides inhibits EB aggregation. Blocking peptides effectively nullifies the function of E-cadherin, as reported by Burdsal et al. (1993). Blocking E-cadherin prevents EBs from adhering with neighboring EBs, thus circumventing subsequent aggregation.

Reducing Inorganic Salt Concentration or Inhibition of Ion Channels

Cell adhesion can be inhibited by substantially reducing inorganic salt concentration (Boraston et al. 1992). For example, cell adhesion modulated by calcium-dependent adhesion molecules such as cadherins depends upon calcium influx from both extracellular calcium through calcium channels and release from internal calcium stores. Calcium channel inhibitor $LaCl_3$ or thapsigargin was shown to inhibit cell-cell attachment (Ko, Arora et al. 2001).

(b) Encapsulation of ES Cells

Figure 8:
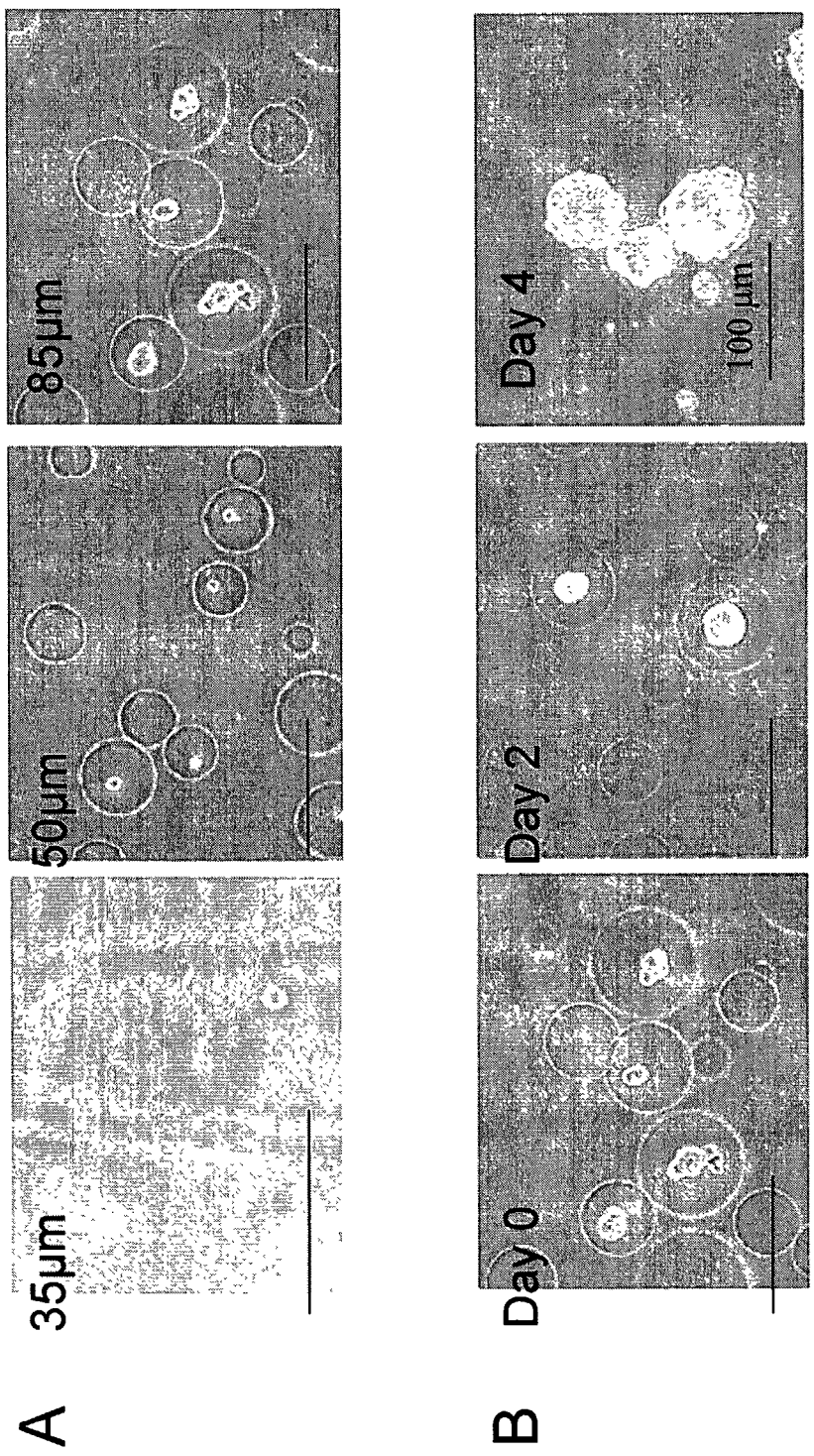
FIG. 8 panel A are photographs of ES cells encapsulated inside agarose microcapsules designed to have specific diameters. Shown are capsules of mean diameter 35 50, and 85 μm. In some capsules single ES cells were encapsulated ((35 and 50 □m capsules), while in other instances, a plurality of ES cells were encapsulated (85 □m capsules).

Preventing EB aggregation was the guiding design principle for new bioprocesses capable of efficient and scalable differentiation of ES cells. While it was suspected that E-cadherin was the main molecule involved in cell aggregation, a method was developed to preclude interactions between all cell-cell adhesion molecules on the EB surface by physically blocking their association. In this method, ES cells are encapsulated within a biodegradable matrix and allowed to grow and differentiate in liquid culture, such that each cell-containing capsule gives rise to a single EB. The surrounding matrix prevents separate EBs from contacting one another, thereby preventing aggregation. Formation of EBs in this novel way permits high cell density culture in a homogeneous, controllable, and scalable bioreactor system. The bioprocess of the present invention is termed: encapsulated stirred culture (ESC). The first step in this method involves the encapsulation of individual or multiple ES cells. Uniform or "synchronized" EB sizes could be achieved by encapsulating similar numbers of ES cells per capsule. The matrix could be agarose, alginate, or another type of natural or artificial matrix (e.g. polymer) that does not interfere with the growth and differentiation of EBs. Depending upon the matrix used, cells might degrade the matrix as they grow (as is the case with agarose), or they might burst the capsule as cell growth places increasing pressure on the capsule (as is the case with alginate), or they can be be manually released from their capsules by adding degradation enzymes (such as agarase addition to agarose), or changing the culture conditions (such as depleting dissolved calcium ions in the case with alginate). Therefore, the size and composition of the capsule can determine the amount of time the EB remains encapsulated. For example, agarose is a simple polysaccharide readily degraded by the cells as they grow. Therefore, the diameter of the agarose capsules determines the amount of time the EB remains encapsulated (FIG. 8.A, Table 3). Capsules are designed to retain the EB until cell differentiation results in downregulation of E-cadherin (or other cell adhesion molecule) expression. After this time, EBs that emerge from the capsules will not aggregate. For differentiating EBs from murine ES cells, E-cadherin is sharply downregulated after 4 days (FIG. 7.A). It was determined that 70-100 μm agarose capsule diameters provide adequate protection for this period of time, and such capsules were specifically designed (FIG. 8.B). However, it should be understood that the invention is not intended to be limited to such a capsule size as a person skilled in the art would appreciate that other sizes would work.

(c) Encapsulation Enables Use of Stirred Culture

ES cells placed directly into stirred culture quickly aggregate into large cell clumps that did not proliferate or differentiate into any of the cell types assayed for (data not shown). Encapsulating ES cells prior to their introduction to stirred culture enabled efficient EB formation and prevented their aggregation. EB efficiency between liquid suspension culture (LSC) [non-stirred, non-encapsulated], stirred culture (SC), and encapsulated stirred culture (ESC) was compared at $10^3$ and $10^4$ input ES cells/ml after 7 days of differentiation culture (Table 4). Whereas EB efficiency in LSC declined as ES cell density increased, EB efficiency remained high in ESC.

Fold expansion of total cells in liquid culture (LSC), stirred culture (SC), and encapsulated stirred culture (ESC) is illustrated in Table 5 Cultures were initiated with $10^4$ R1 ES cells/ml and analyzed after 7 days of differentiation. Table 5 shows results of fold expansion, after adjusting for cell loss during encapsulation procedure. Yield of encapsulated ES cells was approximately 25% of input. Cells were lost during the various transferring stages between centrifuge tubes, or retained in the mineral oil phase.

In stirred culture, EB efficiency was significantly improved with encapsulation than without. Encapsulated ES cells were able to form EBs that remained shielded from one another, thus maintaining a high EB efficiency by preventing EB aggregation. EBs emerged from the capsules after approximately four days—coinciding with down regulation of E-cadherin as previously described. Emerged EBs did not aggregate.

The ability to use stirred or other well-mixed systems ensure that bulk media conditions are homogenous, thus facilitating measurement and control of the system. These culture systems can also accommodate increase demand in cell generation by simply increasing the volume of the tank.

(d) Bioreactor Does Not Significantly Affect Cell Growth or Differentiation

Hematopoietic development within EBs has been extensively studied and well characterized (Keller 1995). Hematopoietic development was therefore selected as the measure by which ES cell differentiation in different culture systems was compared. ES cells become blood cells through a series of developmental steps that can be tracked by cell surface marker expression (Table 6). Murine ES cells differentiate into Flk-1 expressing mesoderm on day 4 that subsequently give rise to CD34 and CD45 expressing hematopoietic progenitor cells. Hematopoietic progenitors can also be assayed for using the hematopoietic colony forming cell (CFC) assay.

Ideally, the encapsulating matrix physically prevents EB aggregation but does not impede transport of nutrients and metabolic products to and from the cells, nor influence differentiation or growth of EBs in any manner. To demonstrate this, ES cells were encapsulated in agarose and differentiated in static liquid culture. Cell proliferation and differentiation in this system was compared to standard ES cell differentiation systems: liquid suspension culture, hanging drop, and methylcellulose cultures. Therefore agarose encapsulation of ES cells did not affect EB cell growth in any significant way.

Cell proliferation and differentiation was also compared between liquid culture (LSC) and the bioprocess enabled by the invention: encapsulated stirred culture (ESC) (Table 7). ESC was able to generate the hematopoietic cell types following the same developmental kinetics as LSC. Cell proliferation and hematopoietic cell frequencies were comparable but not necessarily equivalent between the two systems.

Example 3

Use of Bioprocess to Generate Differentiated Cell Types

Generation of various differentiated cell populations was performed using encapsulated ES cells grown in stirred suspension bioreactors compared to LSC.

a) Generation of Hematopoietic Cells from ES Cells.

Mentioned previously, early mesoderm development was tracked by Flk-1 cell surface marker expression on day 4, while hematopoietic progenitors were detected phenotypically by co-expression of CD34 and CD45 cell surface markers, or functionally via methylcellulose colony assays. Using our novel invention, various types of hematopoietic progenitor cells were detected, from multipotent myeloid cells (CFC- Mix), to further restricted myeloid and erythroid cells (CFC-Ep, CFC-Ed, and CFC-GM) (Table 7). ES cells were differentiated in ES cell media in the absence of LIF. Because the culture was performed in a stirred bioreactor, it is feasibly scalable to any desired volume, and applicable to close microenvironmental control b) Generation of Endothelial Cells from ES Cells.

Figure 9:
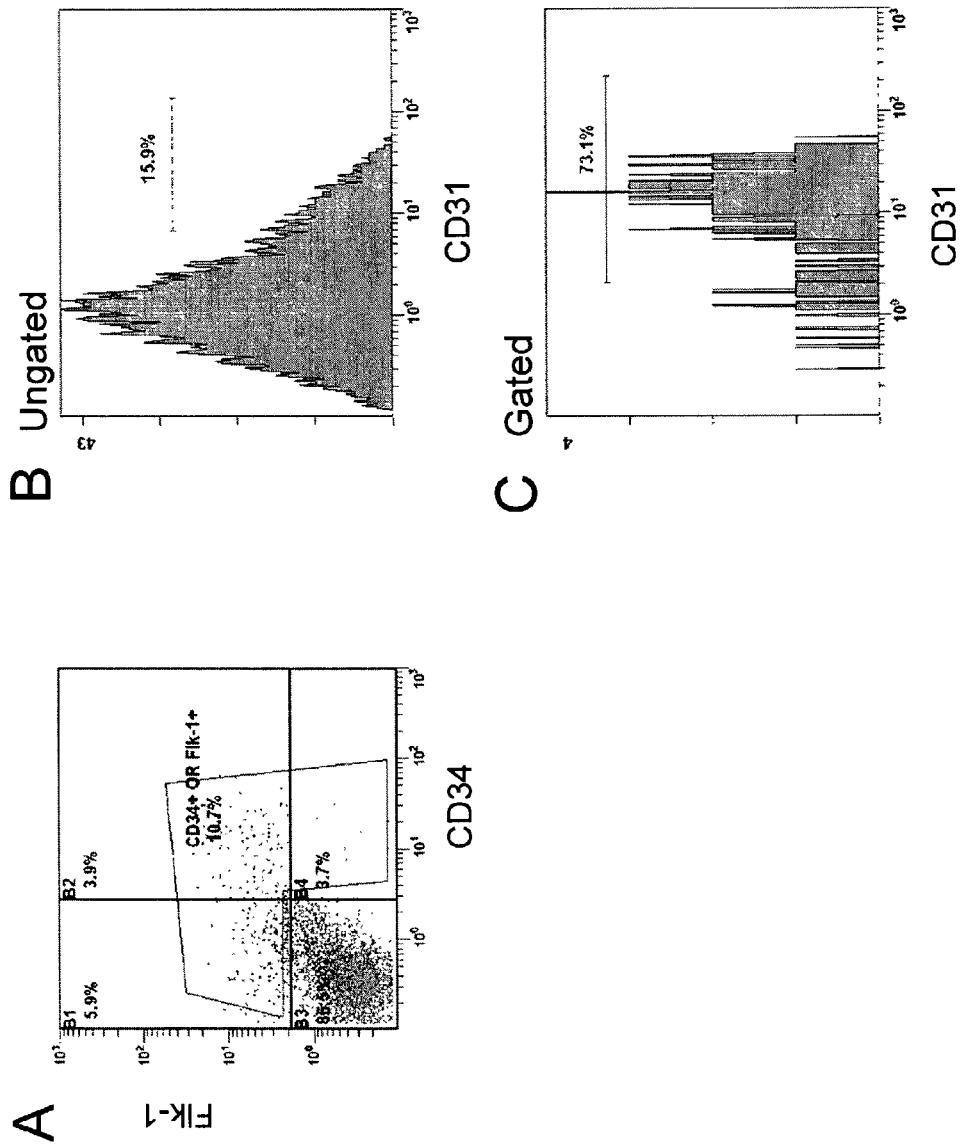
FIG. 9 is a series of flow cytometry plots showing phenotypic detection of endothelial cells generated from encapsulated ES cells grown in stirred suspension bioreactors using flow cytometric based cell surface expression of various endothelial cell markers.

Using the same approach as described above (ES cell differentiated in ES cell media in the absence of LIF) in section a), endothelial cells were detected by coexpression of multiple endothelial cell markers: Flk-1, CD34, and CD31. A gate was drawn around Flk-1 and/or CD34 expressing cells, enabling exclusive analysis of gated cells for expression of CD31 (FIG. 9). Because the culture was performed in a stirred bioreactor, it is feasibly scalable to any desired volume, and applicable to close microenvironmental control.

c) Generation of Other Cell Types from ES Cells

Other researchers have demonstrated that other cell lineages can also be generated from ES cells in vitro, including hepatocytes, β-cells, neurons, glial cells, kidney cells, muscle cells, endothelial cells, hematopoietic cells [i.e., Wang et al, 1992 for endothelial cells; Rohwedel et al., 1994, for cardiac and muscle cells 1994; Bain et al, 1995 for neuronal cells; Palacios et al, 1995 for hematopoietic stem cells; Choi et al, 1998 for hematopoietic and endothelial cells; Fleishman et al, 1998 for cardiac cells; Tropepe et al, 1999 for neural cells], and other cell types known to be derived from ES cells in the art. These cell types can be generated in stirred or mixed bioreactor cultures using media and general environment conditions as described in the prior art, only when aggregation is controlled, such as is possible using the bioprocess of this invention. This would be so as it was demonstrated that the bioprocess of the invention, e.g., encapsulation, does not adversely affect ES cell differentiation. The fact that this technology of the invention allows for the normal differentiation of ES cells, while facilitating the large-scale production of ES cell-derivatives makes it useful for a variety of cellular therapy-related applications.

Example 4

The System Facilitates Measurement and Control of Culture Environment.

Current ES cell differentiation processes are not amenable to measurement and control because the static and batch-style nature of these systems result in spatial and temporal gradients. In well-mixed (dynamic) systems, the bulk media conditions are the same everywhere at any given time. That is, any point measurement made within the system would be reflective of any other point. In this way, one can easily and accurately measure bulk conditions and also introduce control elements.

Using the bioreactor system of Example 2 above, EB development in normoxic (>160 mmHg $O_2$ tension) and hypoxic (30-40 mmHg $O_2$ tension) conditions.was compared. Oxygen tension was measured offline using a blood gas analyzer and gas mixture in the incubator headspace was adjusting accordingly. Hematopoietic cell frequency, determined by CD34 and CD45 expression and hematopoietic CFC assay, was higher for EBs generated in hypoxic conditions (Table 8), indicating the positive effect that the ability to control and manipulate the microenvironment, such as allowed by this invention will have on the generation of cells and tissue from pluripotent cells.

The tendency for ES cells and early EBs to aggregate prevents the use of well-mixed bioreactor systems as well as higher cell density cultures. Therefore current differentiation systems are limited to static and batch-style conditions. The bioprocess of the invention enables ES cells to efficiently form EBs in well-mixed culture by controlling aggregation. As mentioned, the use of well-mixed systems automatically permits bulk media measurements and implementation of control strategies.

Example 5

Figure 10:
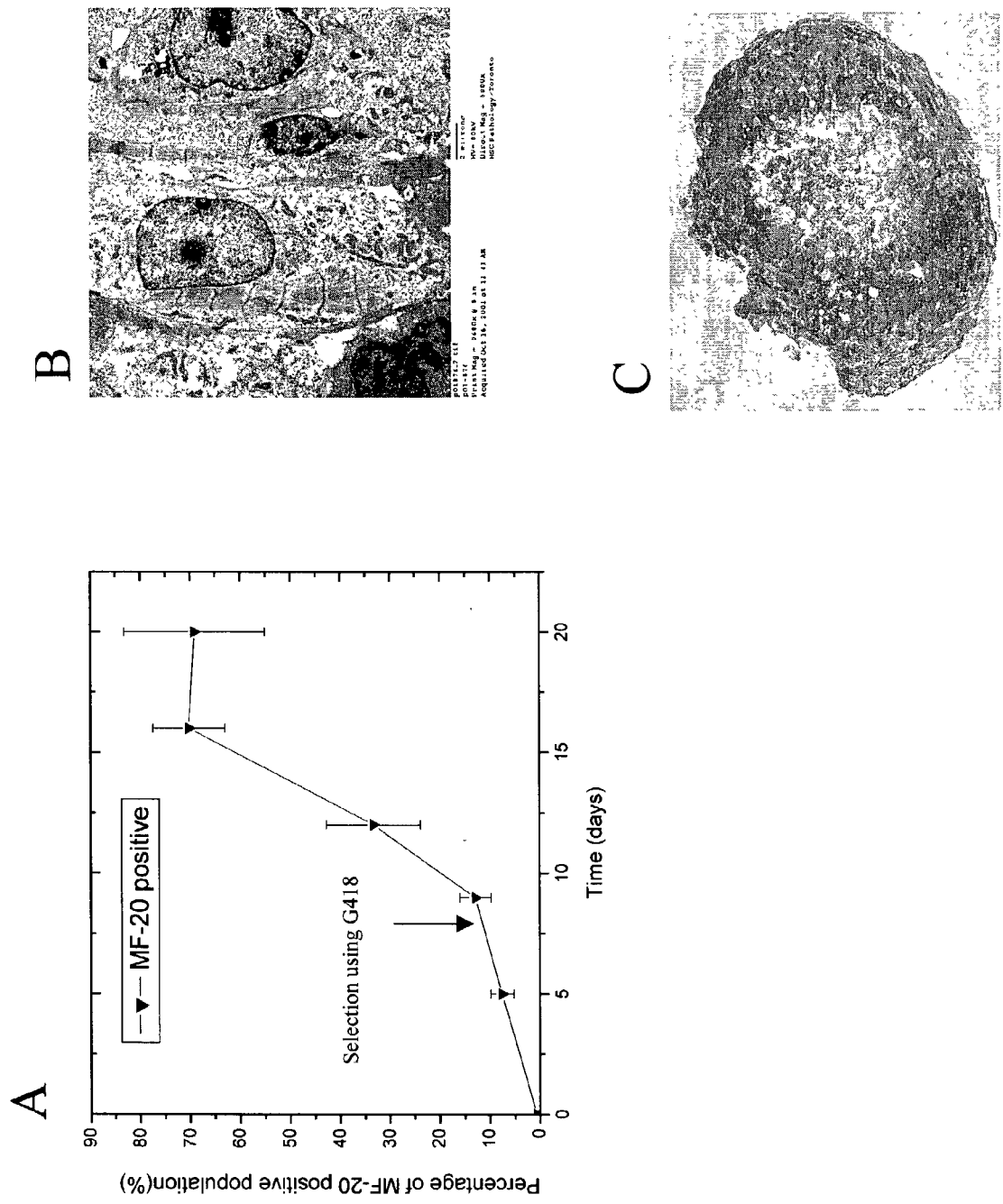
FIG. 10 Panel A shows kinetic changes of the percentage of the MF-20 positive cells during the course of differentiation and selection with G418 of transgene-containing ES cells cultured in stirred suspension bioreactors.

The Generation of Embryonic Stem Cell Derived Cardiac Cells Using ES Cells Transfected with Selectable Markers To demonstrate the improved ability to generate large numbers of clinically relevant cell types, the bioreactor culture of encapsulated ES cells was used to generate and select for cardiac myocytes. As for the above hematopoietic and endothelial development, flow cytometric analysis was employed to quantitatively evaluate the percentage of ES cell-derived cardiomyocytes generated during the course of differentiation in stirred bioreactors. In this case, ES cells transfected with the selection cassette as outlined above and described in detail in (Klug et al 1996, WO 95/14079, May 26, 1995; U.S. Pat. Nos. 5,733,727 and 6,015,671) were cultured for 9 days in 500 mL stirred suspension bioreactors, prior to the addition of G418 to the media. At given time points the EBs were dissociated, the procedure previously described, resulting in a single cell suspension to be stained with a monoclonal antibody specific for sarcromeric myosin heavy chain (MF-20). FIG. 10 Panel A shows kinetic changes of the percentage of the MF-20 positive cells during the course of differentiation and selection with G418 of transgene-containing ES cells cultured in stirred suspension bioreactors. FIG. 10 panel B shows morphologic and structural analysis of bioreactor-grown ES cell-derived cardiomyocytes. The cells exhibit a mature sarcomeric organization and Z-banding (arrow). FIG. 10 panel C shows a cross section of a "cardic body" (a spheroid of ES cell derived cardiac cells) generated in bioreactors.

Results showed that only a trace amount of MF-20 staining-positive cells was present in the EBs (0.7%) on day 0 after differentiation, however, the percentage of cells displaying positive staining with MF-20 rose gradually as a function of time after selection by G418, and reached over 70% at day 20 after differentiation. In contrast, the expression level of Oct-4, which is expressed in embryonic stem cells and is one of the first transcription factors differentially regulated during mouse development (Nichols and Zevnik, 1998) decreased significantly during the time course of differentiation, from 68.5% at day 0 to to undetectable levels (at day 20 after differentiation (data not shown). The observation indicated that at the late state of differentiation and G418 selection, Oct4 positive ES cells were eliminated from the culture system. It is noteworthy that by day 15, the bioreactors typically contained between $2.5 \times 10^7$ to $1 \times 10^8$ viable cardiac myocytes (as assessed by MF20 expression). These observations were consistent in three independent experiments. In some experiments chemical factors such as retinoic acid were added to the media at specific time points to enhance cardiac differentiation and reduce the presence of undifferentiated ES cells (data not shown). The results indicate that differentiation of ES cells with the G418-selection system in spinner flask suspension culture system is capable of producing large quantity of cardiomyocytes.

Example 6

Generation of Chimeric Spheroids Containing Predetermined Types of Cells

To show that the encapsulation system was capable of controlling the types of cells present in the spheroids at input, two populations of R1 ES cells, each labeled with a specific flurochrome (green fluorescent protein, GFP) and (cyan) were encapsulated (see Hadjantonakis et al. 1998 and Hadjantonakis A K, Nagy 2001 for descriptions of the cells lines).

Materials and Methods

Individual R1 ES cells expressing the GFP protein by a constitutively active promoter (Hadjantonakis et al 1998) and individual trophobast stem cells labelled with cyan as previously described (Tanaka et al. 1998) were suspended in Hanks Buffered Saline Solution (HBSS) at a ratio of 1 ES cell to 1 TS cell at a total cell concentration of $2 \times 10^7$ cells/ml and added to a 3% agarose solution for a final cell concentration of $4 \times 10^6$ cells/ml. The agarose solution was dispensed into mineral oil (nonsolvent) at 37° C. and subjected to impeller blending using the One Cell System (Ryan et al., 1995). Micordrops containing a single ES cell and a single TS cell were identified and isolated by their side scatter characteristics, and by their GFP and cyan fluorescence using a FACS-Vantage Flow Cytometer (Becton Dickinson). Isolated microdrops were put sorted into ES cell media without LIF for analysis of their growth characteristics.

EXAMPLE

To show that the encapsulation system was capable of controlling the types of cells present in the spheroids at input, ES cells and TS cells, each labelled with a specific flurochrome (green fluorescent protein, GFP) and cyan were encapsulated as described. Using flow cytometry, the double positive population, (i.e., the microcapsules contained a single GFP cell and a single cyan ˆ labelled cells) were sorted into 96 well plates. Microscope based tracking of the cells confirmed that the two cell types survived and proliferated and formed spheroids containing two distinct sources of cells (chimeric spheroids). This technology provides the capacity to combine, in spheroids, two or more types of cells, including pluripotent cells and differentiated cells, for the end goal of manipulating the differentiation of the pluripotent cells into specific types of tissue using cell specific signals.

Example 7

Formation of ES Cell Derived Neurospheres

ES cells were differentiated in serum-free conditions, yielding spheroids that did not stain for mesoderm markers. ES cells cultured in chemically defined serum-free, feeder layer-free, low-density culture conditions readily acquire a neural identity (Tropepe et al. 1999). Under these conditions, ES cells transition to a spheroid-forming primitive neural stem cell population capable of self-renewal and neural and non-neural potential—analogous to the neurosphere forming neural stem cells reported by Bjornson et al. (1999).

SUMMARY

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims. For instance, although ES cells were used in the Examples, the invention can be applied to other types of pluripotent cell types, such as embryonic germ cells and early primitive ectoderm-like cells or other type of stem cells such as neuronal stem cells or cells that can differentiate into other cell types and form spheroids in vitro during the differentiation process. Controlling aggregation during any type of cell expansion can also be beneficial in improving expansion efficiency of said cell type.

All publications, patents and patent applications are herein incorporated by reference in their entirety to the same extent as if each individual publication, patent or patent application was specifically and individually indicated to be incorporated by reference in its entirety.

TABLE 1

EB formation efficiency from CCE muES cells. A single ES cell was deposited into each well of a 96 well plate. Wells were visually inspected for EBs after 7 days. EB formation efficiency was determined by the ratio of EBs per 96 well plate, to the number of input ES cells per 96 well plate. Percentage of viable ES cells in the culture was determined by E-cadherin expression and exclusion of 7AAD dead cell stain.

| Experiment Number | Input # of ES Cells | # of EBs | Actual EB Formation Efficiency | % Cad Positive Cells | E- Viability | % Viable ES Cells | Calculated EB Formation Efficiency |
|---|---|---|---|---|---|---|---|
| 1 | 86 | 38 | 44.2% | 68.5% | 90% | 61.7% | |
| 2 | 97 | 33 | 34.0% | 85% | 75% | 63.8% | |
| 3 | 68 | 37 | 54.4% | 80% | 96% | 76.8% | |
| 4 | 70 | 26 | 37.1% | — | — | | |
| Average | 80.3 | 33.5 | 42% | 78% | 87% | 68% | 63% |
| Standard Deviation | 13.8 | 5.4 | 9% | 9% | 11% | 14% | 17% |

TABLE 2

Total cell expansion from EBs initiated with 1, 100, or 1000 cells/EB. Cell expansion improved significantly as fewer ES cells were used to initiate EB formation on day 0.

| Initial Cells/EB (day 0) | Maximum Cells/EB | Expansion |
|---|---|---|
| 1 | 17300 ± 9900 | 17300 |
| 100 | 35100 ± 11000 | 351 |
| 1000 | 35000 ± 3000 | 35 |

TABLE 3

Effects of different encapsulation protocols on capsule diameter. 3 different parameters: impeller speed (revolutions per minute, RPM), time (minutes), and ambient temperature, are used to control capsule diameter.

| Protocol step | 35 μm | 50 μm | 85 μm |
|---|---|---|---|
| 1 | 2100 RPM<br>1 minute<br>Room temp | 1500 RPM<br>1 minute<br>Room temp | 1200 RPM<br>1 minute<br>Room temp |
| 2 | 2100 RPM<br>1 minute<br>Ice bath | 1500 RPM<br>1 minute<br>Ice bath | 1200 RPM<br>1 minute<br>Ice bath |
| 3 | 1100 RPM<br>10 minutes<br>Ice bath | 1100 RPM<br>5 minutes<br>Ice bath | 700 RPM<br>5 minutes<br>Ice bath |

TABLE 4

EB Efficiency in liquid culture (LSC), stirred culture (SC), and encapsulated stirred culture (ESC). Cultures were initiated with $10^3$ or $10^4$ CCE ES cells/ml and analyzed after 7 days of differentiation. EB efficiency in LSC declined as cell density increased. Aggregation occurred readily in SC regardless of cell concentration. Encapsulation effectively controlled cell aggregation, maintaining a high EB efficiency in stirred culture.

| | LSC | SC | ESC |
|---|---|---|---|
| $10^3$ ES cell/ml | 42 ± 9% | <0.1% | 41 ± 21% |
| $10^4$ ES cell/ml | 8.5 ± 2.7% | <0.1% | 35 ± 3% |

TABLE 5

Fold expansion of total cells in liquid culture (LSC), stirred culture (SC), and encapsulated stirred culture (ESC). Cultures were initiated with $10^4$ R1 ES cells/ml and analyzed after 7 days of differentiation. The table shows results of fold expansion, after adjusting for cell loss during encapsulation procedure. Yield of encapsulated ES cells was approximately 25% of input. Cells were lost during the various transferring stages between centrifuge tubes, or retained in the mineral oil phase.

| | LSC | SC | ESC |
|---|---|---|---|
| $10^4$ ES cells/ml | 27 ± 13 | <1 | 63 ± 33 |

TABLE 6

Hematopoietic and endothelial cell surface markers.

| | |
|---|---|
| Flk-1 | Vascular endothelial growth factor receptor expressed by early mesoderm, vascular progenitor, and endothelial cells. |
| CD34 | Antigen expressed by hematopoietic stem, hematopoietic progenitor, and endothelial cells. |

TABLE 6-continued

Hematopoietic and endothelial cell surface markers.

| | |
|---|---|
| CD45 | Antigen expressed by hematopoietic cells |
| CD31 | Cell adhesion molecule expressed by platelets, endothelial cells, and murine ES cells. |

TABLE 7

Comparison of cell proliferation and differentiation between standard ES cell differentiation culture: liquid culture (LSC), and bioprocess of the invention: encapsulated stirred culture (ESC). Proliferation reported as total cells per EB. Flk-1 expressing mesoderm with hematopoietic potential was assayed on day 4 of differentiation culture. Hematopoietic progenitors coexpressing CD34 and CD45, and/or capable of hematopoietic colony formation (CFC) were assayed on day 7.

| Analysis | LSC | ESC |
|---|---|---|
| Day 4 - Mesoderm | | |
| Total Cells/EB | 700 ± 300 | 1200 ± 450 |
| Flk-1+ cells | 44 ± 12% | 38 ± 8% |
| Day 7 - Hematopoietic | | |
| Total Cells/EB | 3000 ± 1500 | 3500 ± 700 |
| CD34+CD45+ cells | 1.9 ± 1.2% | 1.0 ± 0.6% |
| CFCs per $10^5$ cells | 14.0 ± 6.0 | 5.0 ± 2.0 |

TABLE 8

Comparison of hematopoietic cell development (on day 7 of differentiation culture) between normoxic (>160 mmHg $O_2$) and hypoxic (30-40 mmHg $O_2$) encapsulated stirred culture (ESC).

| Analysis (Day 7) | Normoxic ESC | Hypoxic ESC |
|---|---|---|
| Total CD34+ cells | 6.1% | 8.0% |
| Total CD45+ cells | 0.9% | 2.6% |
| CD34+CD45+ cells | 0.6% | 1.6% |
| CFCs per $10^5$ cells | 5 ± 2.0 | 7 ± 2.6 |

TABLE 9

Cell Lineage-Specific Promoters

| Promoter | Obtained Cell Lineage | Literature |
|---|---|---|
| α-cardiac myosin heavy chain promoter | cardiomyocytes | Klug et al. (1996) J. Clin. Invest. 98: 216-24 |
| MLC-2v | cardiomyocytes | Muller et al. (2000) FASEB J. 2000 Dec.; 14(15): 2540-8 |
| human atrial natriuretic factor (hANF) promoter | cardiomyocytes | Wu et al. (1989) J. Biol. Chem. 264: 6472-79 |
| SOX2 gene | neural precursors | Li et al. (1998) Curr. Biol. 8: 971-4 |
| Human insulin promoter (HIP) | Beta cells (insulin-secreting cells) | Soria et al. (2000) Diabetes 49: 157 |
| PDX1 promoter | Beta cells (insulin-secreting cells) pancreatic cells | Gannon M. et al. (2001) Dev Biol. 2001 Oct. 1; 238(1): 185-201 |
| Pax4 promoter | Beta cells (insulin-secreting cells) | Brink C. et al. (2001) Mech Dev. 2001 Jan.; 100(1): 37-43, Smith SB. et al. (2000) J Biol Chem. 2000 Nov. 24; 275(47): 36910-9. |
| VE-Cadherin promoter | Endothelial cells | Gory S. et al. (1999) Blood. 1999 Jan. 1; 93(1): 184-92. |
| human VE-Cadherin-2 promoter | Endothelial cells | Ludwig D. et al. (2000) Mamm Genome. 2000 Nov.; 11(11): 1030-3 |

TABLE 10

Examples of cell types derived from the in vitro differentiation of ES cells, as well as examples of additives thought to encourage the differentiation/survival of the specific cell types are indicated. In most cases the additive is added to serum containing media; examples of cells generated in a Chemically Defined Media (CDM) are also listed.

| Cell Type Generated | Example Additives | Reference |
|---|---|---|
| Primitive ectoderm | CDM | Tropepe et al. 2001 |
| Mesoderm precursors | BMP4, Activin A | Wiles et al. 1999 |
| Endothelial cells | VEGF | Eichmann et al. 1997 |
| Hematopoietic cells | IL-11 + KL, IL-1 | Keller et al. 1993 |
|  | VEGF + KL | Kennedy et al. 1997 |
|  | VEGF + BMP4 | Nakayama et al. 2000 |
|  | IL-2 + IL-3 + Con A | Chen et al. 1992 |
| Erythroid cells | Epo | Wiles et al. 1991 |
| Myeloid cell | IL-3 + IL-1 + Epo, IL-3 + IL-1 + M-CSF/GM-CSF IL-3 + M-CSF | Wiles et al. 1991 Lieschke et al. 1995 |
| Lymphoid cells | VEGF + BMP4 RP.0.010 + IL3 + IL-6 + IL-11 | Nakayama et al. 2000 Gutierrez-Ramos et al. 1992 |
| Skeletal muscle | TGFβ1/TGFβ2 DMSO | Slager et al. 1993 Dinsmore et al. 1996 |
| Cardiac muscle | TGFβ1/TGFβ2 RA | Slager et al. 1993 Wobus et al. 1997 |
| Neuroectoderm | CDM NGF bFGF | Tropepe et al. 2001 Yamada et al. 1994 Okabe et al. 1996 |
| Neurons | RA | Bain et al. 1995 |
| Adipocytes | RA + insulin + T3 | Dani et al. 1997 |
| Beta-cells | B27 Supplement & bFGF B27 Supplement & Nikotinamid | Lumelsky NO. et al. 2001 |
| Beta-cells | Nikotinamid | Soria B. et al. 2000 |
| Beta-cells | EGF, HGF and Nikotinamid | Ramiva VKM. et al. 2000 |

TABLE 11

Examples of cell types derived from the in vitro differentiation of human embryonic stem cells, as well as examples of additives thought to encourage the differentiation/survival of the specific cell types are indicated.

| Cell Type Generated | Example Additives | Reference |
|---|---|---|
| Mesodermal cells | Activin-A and TGFbeta1 | Schuldiner M, et al. 2000 |
| Ectodermal, Mesodermal cells | Retinoic acid (RA), EGF, BMP-4, bFGF | Schuldiner M, et al. 2000 |
| Ectodermal, Mesodermal Endodermal cells | NGF and HGF | Schuldiner M, et al. 2000 |
| Neuronal cells | Retinoic acid (RA), nerve growth factor (betaNGF) sodium butyrate | Schuldiner M, et al. 2001 |
| Hepatocytes |  | Rambhatla L, .et al. 2001 |
| Beta-cells |  | Assady S, et al. 2001 |
| Cardiomyocytes |  | Kehat I, et al. 2001 |
| Endothelial cells |  | Levenberg S, et al. 2002 |

FULL CITATIONS FOR REFERENCES REFERRED TO IN THE SPECIFICATION

1. Assady S, Maor G, Amit M, Itskovitz-Eldor J, Skorecki K L, Tzukerman M. 2001 Diabetes Insulin production by human embryonic stem cells. 50(8):1691-7.
2. Bain, G., D. Kitchens, et al. (1995). "Embryonic stem cells express neuronal properties in vitro." Dev Biol 168(2): 342-57.
3. Bain G, Ray W J, Yao M, Gottlieb D I: Retinoic acid promotes neural and represses mesodermal gene expression in mouse embryonic stem cells in culture. Biochem Biophys Res Commun 223:691, 1996.
4. Beddington R S, Robertson E J. 1989 An assessment of the developmental potential of embryonic stem cells in the midgestation mouse embryo. Development 105(4):733-7.
5. Bjornson C R, Rietze R L, Reynolds B A, Magli M C, Vescovi A L; Turning brain into blood: a hematopoietic fate adopted by adult neural stem cells in vivo. Science 283: 534-7, 1999.
6. Boraston R, Marshall C, Norman P, Renner G, Warner J; Elimination of cell aggregation in suspension culture of Chinese hamster ovary (CHO)cells. In: R. E. Spier, J. B. Griffiths, and C. MacDonald (eds.), Animal cell technology: Developments, processes and products. Butterworth-Heinemann, Oxford 1992.
7. Brink C, Chowdhury K, Gruss P. Pax4 regulatory elements mediate beta cell specific expression in the pancreas. Mech Dev. January 2001;100(1):37-43.
8. Burdsal, C. A., Damsky, C. H., and Pedersen, R. A. The role of E-cadherin and integrins in mesoderm differentiation and migration at the mammalian primitive streak. Development, 118: 829-844 (1993).
9. Chen U, Kosco M, Staerz U: Establishment and characterization of lymphoid and myeloid mixed-cell populations from mouse late embryoid bodies, "embryonic-stem-cell fetuses". Proc Natl Acad Sci USA 89:2541, 1992.
10. Choi, K., M. Kennedy, et al. (1998). "A common precursor for hematopoietic and endothelial cells." *Development* 125(4): 725-32.
11. Clarke D L, Johansson C B, Wilbertz J, Veress B, Nilsson E, Karlstrom H, Lendahl U, Frisen J. (2000) Generalized potential of adult neural stem cells. *Science* 288(5471): 1660-3.
12. Dang S M, Kyba M, Perlingeiro R, Daley G Q, Zandstra P W 2002 Efficiency of embryoid body formation and hematopoietic development from embryonic stem cells in different culture systems. Biotechnol Bioeng 78(4):442-53.
13. Dani C, Smith A G, Dessolin S, Leroy P, Staccini L, Villageois P, Darimont C, Ailhaud G: Differentiation of embryonic stem cells into adipocytes in vitro. J Cell Sci 110 (Pt 11): 1279, 1997.
14. Dickson M C, Slager H G, Duffie E, Mummery C L, and Akhurst R J. RNA and protein localisations of TGF beta 2 in the early mouse embryo suggest an involvement in cardiac development. Development, 117(2):625-39 (1993).
15. Dinsmore J, Ratliff J, Deacon T, Pakzaban P, Jacoby D, Galpern W, Isacson O: Embryonic stem cells differentiated in vitro as a novel source of cells for transplantation. Cell Transplant 5:131, 1996.
16. Doetschman T C, Eistetter H, Katz M, Schmidt W, Kemler R: The in vitro development of blastocyst-derived embryonic stem cell lines: formation of visceral yolk sac, blood islands and myocardium. J Embryol Exp Morphol 87:27, 1985.
17. Eichmann A, Corbel C, Nataf V, Vaigot P, Breant C, Le Douarin N M: Ligand-dependent development of the endothelial and hemopoietic lineages from embryonic mesodermal cells expressing vascular endothelial growth factor receptor 2. Proc Natl Acad Sci USA 94:5141, 1997.
18. Evans, M. J. and M. H. Kaufman (1981). "Establishment in culture of pluripotential cells from mouse embryos." *Nature* 292(5819): 154-6.
19. Fleischmann, M., W. Bloch, et al. (1998). "Cardiac specific expression of the green fluorescent protein during early murine embryonic development." *FEBS Lett* 440(3): 370-6.
20. Gannon M, Gamer L W, Wright C V. Regulatory regions driving developmental and tissue-specific expression of the essential pancreatic gene pdx1. Dev Biol. Oct. 1, 2001; 238(1):185-201.
21. Lieschke G J, Dunn A R: Development of functional macrophages from embryonal stem cells in vitro. Exp Hematol 23:328, 1995.
22. Gory S, Vernet M, Laurent M, Dejana E, Dalmon J, Huber P. The vascular endothelial-cadherin promoter directs endothelial-specific expression in transgenic mice. Blood. Jan. 1, 1999;93(1):184-92.
23. Gutierrez-Ramos J C, Palacios R: In vitro differentiation of embryonic stem cells into lymphocyte precursors able to generate T and B lymphocytes in vivo. Proc Natl Acad Sci USA 89:9171, 1992.
24. Hadjantonakis A K, Gertsenstein M, Ikawa M, Okabe M, Nagy A. 1998 Generating green fluorescent mice by germline transmission of green fluorescent ES cells Mech Dev August;76(1-2):79-90.
25. Hadjantonakis A K, Nagy A. The color of mice: in the light of GFP-variant reporters 2001.Histochem Cell Biol 115(1):49-58.
26. Irvine D J, Mayes A M, Satija S K, Barker J G, Sofia-Allgor S J, Griffith L G., Comparison of tethered star and linear poly(ethylene oxide) for control of biomaterials surface properties. J Biomed Mater Res Jun. 5, 1998;40(3): 498-509.
27. Jones J M, Thomson J A, Human embryonic stem cell technology, Semin Reprod Med 2000;18(2):219-23.
28. Kalyani A, Hobson K, Rao M S. (1997) Neuroepithelial stem cells from the embryonic spinal cord: isolation, characterization, and clonal analysis. Dev Biol 186(2):202-23.
29. Kehat I, Kenyagin-Karsenti D, Snir M, Segev H, Amit M, Gepstein A, Livne E, Binah O, Itskovitz-Eldor J, Gepstein L. Human embryonic stem cells can differentiate into myocytes with structural and functional properties of cardiomyocytes. J Clin Invest. August 2001;108(3):407-14.
30. Keller, G. M. (1995). "In vitro differentiation of embryonic stem cells." Curr Opin Cell Biol 7(6): 862-9.
31. Keller G, Kennedy M, Papayannopoulou T, Wiles M V: Hematopoietic commitment during embryonic stem cell differentiation in culture. Mol Cell Biol 13:473, 1993.
32. Kennedy M, Firpo M, Choi K, Wall C, Robertson S, Kabrun N, Keller G: A common precursor for primitive erythropoiesis and definitive haematopoiesis. Nature 386: 488, 1997.
33. Klug M G, Soonpaa M H, Koh G Y, Field L J., Genetically selected cardiomyocytes from differentiating embryonic stem cells form stable intracardiac grafts, J Clin Invest Jul. 1, 1996;98(1):216-24.
34. Klug, M. G., M. H. Soonpaa, et al. (1996). "Genetically selected cardiomyocytes from differentiating embronic stem cells form stable intracardiac grafts." J Clin Invest 98(1): 216-24.

35. Ko K S, Arora P D, Bhide V, Chen A, McCulloch C A; Cell-cell adhesion in human fibroblasts requires calcium signaling. J Cell Sci 114:1155-67, 2001.
36. Larue, L., Antos, C., Butz, S., Huber, O., Delmas, V., Dominis, M., and Kemler, R. A role for cadherins in tissue formation. Development, 122: 3185-3194 (1996).
37. Li M, Pevny L, Lovell-Badge R, Smith A. Generation of purified neural precursors from embryonic stem cells by lineage selection. Curr Biol. Aug. 27, 1998;8(17):971-4.
38. Levenberg S, Golub J S, Amit M, Itskovitz-Eldor J, Langer R. 2002 Endothelial cells derived from human embryonic stem cells. Proc Natl Acad Sci USA 99(7): 4391-6.
39. Ludwig D, Lorenz J, Dejana E, Bohlen P, Hicklin D J, Witte L, Pytowski B. cDNA cloning, chromosomal mapping, and expression analysis of human VE-Cadherin-2. Mamm Genome. November 2000;11(11):1030-3.
40. Lumelsky, N., O. Blondel, P. Laeng, I. Velasco, R. Ravin, and R. McKay. 2001. Differentiation of embryonic stem cells to insulin-secreting structures similar to pancreatic islets. Science 292:1389.
41. Maltepe E, Schmidt J V, Baunoch D, Bradfield C A, Simon M C 1997Nature Abnormal angiogenesis and responses to glucose and oxygen deprivation in mice lacking the protein ARNT 386(6623):403-7.
42. Marshall, E. The business of stem cells. Science, 287 (5457): 1419-1421 (2000).
43. McKinney-Freeman S L, Jackson K A, Camargo F D, Ferrari G, Mavilio F, Goodell M A. 2002 Muscle-derived hematopoietic stem cells are hematopoietic in origin.Proc Natl Acad Sci USA 99(3):1341-6.
44. Muller M, Fleischmann B K, Selbert S, Ji G J, Endl E, Middeler G, Muller O J, Schlenke P, Frese S, Wobus A M, Hescheler J, Katus H A, Franz W M. Selection of ventricular-like cardiomyocytes from ES cells in vitro. FASEB J. December 2000;14(15):2540-8.
45. Mummery C, Ward D, van den Brink C E, Bird S D, Doevendans P A, Opthof T, Brutel de la Riviere A, Tertoolen L, van der Heyden M, Pera M. 2002 J Anat Cardiomyocyte differentiation of mouse and human embryonic stem cells. 200(Pt 3):233-42.
46. Nakayama N, Lee J, Chiu L: Vascular endothelial growth factor synergistically enhances bone morphogenetic protein-4-dependent lymphohematopoietic cell generation from embryonic stem cells in vitro. Blood 95:2275, 2000.
47. Nagy A, Rossant J, Nagy R, Abramow-Newerly W, Roder J C. 1993 Derivation of completely cell culture-derived mice from early-passage embryonic stem cells.Proc Natl Acad Sci USA 90(18):8424-8.
48. Nichols J, Zevnik B, Anastassiadis K, Niwa H, Klewe-Nebenius D, Chambers I, Scholer H, Smith A. 1998 Formation of pluripotent stem cells in the mammalian embryo depends on the POU transcription factor Oct4. Cell 95(3): 379-91.
49. Okabe S, Forsberg-Nilsson K, Spiro A C, Segal M, McKay R D: Development of neuronal precursor cells and functional postmitotic neurons from embryonic stem cells in vitro. Mech Dev 59:89, 1996
50. Palacios, R., E. Golunski, et al. (1995). "In vitro generation of hematopoietic stem cells from an embryonic stem cell line." *Proc Natl Acad Sci USA* 92(16): 7530-4.
51. Pelton T A, Sharma S, Schulz T C, Rathjen J, Rathjen P D. 2002 Transient pluripotent cell populations during primitive ectoderm formation: correlation of in vivo and in vitro pluripotent cell development.J Cell Sci 115(Pt 2):329-39.
52. Perkins A C; Enrichment of blood from embryonic stem cells in vitro. Reprod Fertil Dev 10:563-72, 1998.
53. Rambhatla L, Carpenter M K, Kundu P, Huang L, Chiu C P. Derivation of Hepatocyte like Cells from Human Embryonic Stem Cells, Abstract Book Keystone Symposia on Pluripotent Stem Cells: Biology and application. Sheraton Tamarron Resort, Durango, Colo. Feb. 6-11, 2001; Poster number: 326
54. Ramiya, V. K., M. Maraist, K. E. Arfors, D. A. Schatz, A. B. Peck, and J. G. Cornelius. 2000. Reversal of insulin-dependent diabetes using islets generated in vitro from pancreatic stem cells. Nat Med 6:278.
55. Rathjen, P. D., Lake, J., Whyatt, L. M., Bettes, M. D., and Rathjen, J. Properties and uses of embryonic stem cells: prospects for application to human biology and gene therapy. Reproduction, Fertility, Development, 10: 31-47 (1998)
56. Rohwedel, J., V. Maltsev, et al. (1994). "Muscle cell differentiation of embryonic stem cells reflects myogenesis in vivo: developmentally regulated expression of myogenic determination genes and functional expression of ionic currents." *Dev Biol* 164(1): 87-101.
57. Reubinoff B E, Itsykson P, Turetsky T, Pera M F, Reinhartz E, Itzik A, Ben-Hur T. 2001 Neural progenitors from human embryonic stem cells. Nat Biotechnol 19(12):1134-40
58. Ryan, C, Nguyen, B., et al. (1995). "Rapid Assay for Mycobacterial Growth and Antibiotic Susceptibility Using Gel Microdrop Encapsulation." *J. Clin. Microbiology* 33(7):1720-1726.
59. Schwartz R E, Reyes M, Koodie L, Jiang Y, Blackstad M, Lund T, Lenvik T, Johnson S, Hu W S, Verfaillie C M. (2002). "Multipotent adult progenitor cells from bone marrow differentiate into functional hepatocyte-like cells." J Clin Invest 109(10):1291-302.
60. Schuldiner M, Yanuka O, Itskovitz-Eldor J, Melton D A, Benvenisty N. Effects of eight growth factors on the differentiation of cells derived from human embryonic stem cells. Proc Natl Acad Sci USA. Oct. 10, 2000;97(21):11307-12.
61. Schuldiner M, Eiges R, Eden A, Yanuka O, Itskovitz-Eldor J, Goldstein R S, Benvenisty N. Induced neuronal differentiation of human embryonic stem cells. Brain Res. Sep. 21, 2001;913(2):201-5.
62. Sefton M V, Hwang J R, Babensee J E. Selected aspects of the microencapsulation of mammalian cells in HEMA-MMA. Ann NY Acad Sci., 831:260-70 (1997)
63. Slager H G, Van Inzen W, Freund E, Van den Eijnden-Van Raaij A J, Mummery C L: Transforming growth factor-beta in the early mouse embryo: implications for the regulation of muscle formation and implantation. Dev Genet 14:212, 1993
64. Smith S B, Watada H, Scheel D W, Mrejen C, German M S. Autoregulation and maturity onset diabetes of the young transcription factors control the human PAX4 promoter. J Biol Chem. Nov. 24, 2000;275(47):36910-9.
65. Soria B. 2001 In-vitro differentiation of pancreatic beta-cells. Differentiation 68(4-5): 205-19.
66. Soria, B., A. Skoudy, et al. (2001). "From stem cells to beta cells: new strategies in cell therapy of diabetes mellitus." Diabetologia 44(4): 407-15
67. Soria, B., E. Roche, et al. (2000). "Insulin-secreting cells derived from embryonic stem cells normalize glycemia in streptozotocin-induced diabetic mice." Diabetes 49(2): 157-62.
68. Soria, B., E. Roche, G. Berna, T. Leon-Quinto, J. A. Reig, and F. Martin. 2000. Insulin-secreting cells derived from embryonic stem cells normalize glycemia in streptozotocin-induced diabetic mice. Diabetes 49:157.

69. Suzuki A, Zheng Y W, Kaneko S, Onodera M, Fukao K, Nakauchi H, Taniguchi H. 2002 Clonal identification and characterization of self-renewing pluripotent stem cells in the developing liver. J Cell Biol 156(1):173-84
70. T Tanaka S, Kunath T, Hadjantonakis A K, Nagy A, Rossant J. Promotion of trophoblast stem cell proliferation by FGF4. 1998 Science 282(5396):2072-5
71. Thomson, J. A., J. Itskovitz-Eldor, et al. (1998). "Embryonic stem cell lines derived from human blastocysts." *Science* 282(5391): 1145-7.
72. Thomson J A, Odorico J S. 2000 Human embryonic stem cell and embryonic germ cell lines.Trends Biotechnol 18(2):53-7.
73. Toma J G, Akhavan M, Fernandes K J, Barnabe-Heider F, Sadikot A, Kaplan D R, Miller F D. 2001 Isolation of multipotent adult stem cells from the dermis of mammalian skin. Nat Cell Biol September;3(9):778-84
74. Tropepe V, Hitoshi S, Sirard C, Mak T W, Rossant J, van der Kooy D: Direct neural fate specification from embryonic stem cells: a primitive mammalian neural stem cell stage acquired through a default mechanism. Neuron 30:65, 2001
75. Tropepe, V., M. Sibilia, et al. (1999). "Distinct neural stem cells proliferate in response to EGF and FGF in the developing mouse telencephalon." *Dev Biol* 208(1): 166-88.
76. Turcanu V, Williams N A: Cell identification and isolation on the basis of cytokine secretion: a novel tool for investigating immune responses. Nat Med 7:373, 2001
77. Vallbacka J J, Nobrega J N, Sefton M V., Tissue engineering as a platform for controlled release of therapeutic agents: implantation of microencapsulated dopamine producing cells in the brains of rats., J Control Release May 14, 2001;72(1-3):93-100
78. Wang, R., R. Clark, et al. (1992). "Embryonic stem cell-derived cystic embryoid bodies form vascular channels: an in vitro model of blood vessel development." Development 114(2): 303-16.
79. Wartenberg M, Gunther J, Hescheler J, Sauer H. Lab Invest 1998 The embryoid body as a novel in vitro assay system for antiangiogenic agents. 78(10):1301-14
80. Weaver, J. C, Williams, G. B., Klibanov, A., and Demain, A. L. Gel microdroplets: rapid detection and enumeration of individual microorganisms by their metabolic activity. Biotechnology, 6: 1084-1089 (1988)
81. Wiles, M. V. and Johansson, B. M. Embryonic stem cell development in chemically defined medium. Experimental Cell Research, 247: 241-248 (1999)
82. Wiles M V, Keller G: Multiple hematopoietic lineages develop from embryonic stem (ES) cells in culture. Development 111:259, 1991
83. Wobus A M, Kaomei G, Shan J, Wellner M C, Rohwedel J, Ji G, Fleischmann B, Katus H A, Hescheler J, Franz W M: Retinoic acid accelerates embryonic stem cell-derived cardiac differentiation and enhances development of ventricular cardiomyocytes. J Mol Cell Cardiol 29:1525, 1997
84. Wu J, LaPointe M C, West B L, Gardner D G.Tissue-specific determinants of human atrial natriuretic factor gene expression in cardiac tissue. J Biol Chem. Apr. 15, 1989;264(11):6472-9.
85. Yamada G, Kioussi C, Schubert F R, Eto Y, Chowdhury K, Pituello F, Gruss P: Regulated expression of Brachyury(T), Nkx1.1 and Pax genes in embryoid bodies. Biochem Biophys Res Commun 199:552, 1994
86. Zandstra, P. W., Conneally, E., Petzer, A. L., Piret, J. M., and Eaves, C. J., "Cytokine manipulation of primitive human hematopoietic cell self-renewal",. Proc. Natl. Acad. USA, 94:4698-4703, 1997
87. Zandstra P W, Nagy A. 2001Stem cell bioengineering. Annu Rev Biomed Eng 3:275-305.
88. Zandstra, P. W., D. A. Lauffenburger, et al. (2000). "A ligand-receptor signaling threshold model of stem cell differentiation control: a biologically conserved mechanism applicable to hematopoiesis." Blood 96(4): 1215-22.

What is claimed is:

1. A bioprocess for controlling aggregation of embryoid bodies during differentiation, comprising:
   a) monitoring E-cadherin expression over time in a differentiating embryoid body;
   b) determining a time when E-cadherin is down-regulated sufficiently in said embryoid body to prevent aggregation of embryoid bodies;
   c) encapsulating one or more embryonic stem cells expressing E-cadherin in a biodegradable matrix so as to form a cell capsule, wherein the capsule is of a size to enable an embryoid body formed within the capsule to emerge from the capsule after down regulation of E-cadherin;
   d) introducing the encapsulated cells into a cell culture environment comprising cell culture media, growth factors, and other factors to promote cell growth;
   e) culturing the encapsulated cells from d) so as to form an embryoid body, said culturing being for a time as determined in b), such that the embryoid body formed within the capsule will emerge from the capsule and will not aggregate with other embryoid bodies upon emergence from the capsule;
   f) optionally harvesting differentiated cells derived from the embryoid body that emerged from the capsule from the culture in step e).

2. The bioprocess of claim 1, wherein the matrix is agarose or alginate.

3. The bioprocess of claim 1, wherein the capsules are between 35 and 85 μm in diameter.

4. The bioprocess of claim 1, wherein the cell culture environment is a stirred bioreactor.

5. The bioprocess of claim 1, wherein the cells are cultured at a density of at least $10^5$ cells per mL.

6. The bioprocess of claim 1, wherein the cell culture media contains bovine serum or retinoic acid.

7. The bioprocess of claim 1, which is part of a bioprocess for producing hematopoietic cells, neural cells, endothelial cells, or cardiomyocytes.

8. The bioprocess of claim 1, further comprising determining expression of cell surface markers by the harvested differentiated cells of step (f).

9. The bioprocess of claim 1, further comprising selecting a desired differentiated cell type according to its phenotype.

10. The bioprocess of claim 9, wherein the differentiated cells are selected using a promoter-reporter construct introduced into the differentiated cells.

11. The bioprocess of claim 1, further comprising determining functional activity of the differentiated cells in a methylcellulose colony assay.

12. The bioprocess of claim 1, further comprising harvesting hematopoietic or endothelial cells from the culture.

13. The bioprocess of claim 1, further comprising harvesting cardiac myocytes from the culture.

14. The bioprocess of claim 13, wherein the harvested cells are over 70% positive for MF-20.

15. The bioprocess of claim 1 wherein cell differentiation continues after the embryoid body emerges from the capsule.

16. The bioprocess of claim 1 wherein the capsule holds up to 35,000 cells.

17. The bioprocess of claim 2 wherein the capsule holds up to 4200 cells at time of emergence of the embryoid body.

18. The bioprocess of claim 1, wherein in step (c), 1-1000 embryonic stem cells are initially encapsulated in one capsule.

19. The process of claim 1, wherein steps (a) to (e) are done in a static culture, and wherein the embryoid body is transferred to a stirred bioreactor after step (e) and before step (f).

20. The bioprocess of claim 1 wherein the time E-cadherin is down-regulated to prevent aggregation of embryoid bodies is 4 days.

21. The bioprocess of claim 20, wherein the embryoid bodies are produced from mouse ES cells.

22. The bioprocess of claim 21 wherein the capsule is 70-100 μm in diameter.

* * * * *